(12) United States Patent
Kim et al.

(10) Patent No.: US 8,795,994 B2
(45) Date of Patent: Aug. 5, 2014

(54) METHOD OF PRODUCING BIOFUEL USING SEA ALGAE

(75) Inventors: Gyung Soo Kim, Yongin-si (KR);
Myung-Kyo Shin, Seoul (KR); Yong Jin Kim, Youngin-si (KR); Kyeong Keun Oh, Seongnam-si (KR); Jun Seok Kim, Seongnam-si (KR); Hyun Jin Ryu, Cheonan-si (KR); Key Hyup Kim, Seoul (KR)

(73) Assignee: Korea Institute of Industrial Technology, Chungcheongnam-Do (KR)

( * ) Notice: Subject to any disclaimer, the term of this patent is extended or adjusted under 35 U.S.C. 154(b) by 726 days.

(21) Appl. No.: 12/528,598

(22) PCT Filed: Feb. 26, 2008

(86) PCT No.: PCT/KR2008/001102
§ 371 (c)(1),
(2), (4) Date: Dec. 9, 2009

(87) PCT Pub. No.: WO2008/105618
PCT Pub. Date: Sep. 4, 2008

(65) Prior Publication Data
US 2010/0124774 A1   May 20, 2010

(30) Foreign Application Priority Data

Feb. 26, 2007 (KR) .......................... 10-2007-0018867
Jul. 13, 2007 (KR) .......................... 10-2007-0070687
Jul. 27, 2007 (KR) .......................... 10-2007-0076030

(51) Int. Cl.
*C12P 7/06* (2006.01)
*C12P 7/08* (2006.01)
*C12P 7/16* (2006.01)
*C12P 7/04* (2006.01)
*C12P 7/26* (2006.01)
*C12P 7/28* (2006.01)

(52) U.S. Cl.
USPC ........... 435/161; 435/148; 435/150; 435/157; 435/160

(58) Field of Classification Search
None
See application file for complete search history.

(56) References Cited

U.S. PATENT DOCUMENTS

| 3,901,873 | A |   | 8/1975  | Doi |           |
|-----------|---|---|---------|-----|-----------|
| 4,376,163 | A |   | 3/1983  | Ehnstrom |     |
| 5,100,791 | A |   | 3/1992  | Spindler et al. | |
| 5,231,017 | A |   | 7/1993  | Lantero |      |
| 5,843,762 | A | * | 12/1998 | Moll | 435/257.1 |
| 6,509,180 | B1|   | 1/2003  | Verser |       |
| 7,067,303 | B1|   | 6/2006  | Nichols |      |

| 2007/0250961 | A1 | * | 10/2007 | Blaylock et al. | 800/283 |
| 2010/0064746 | A1 | * | 3/2010  | Medoff | 71/8 |
| 2011/0136189 | A1 | * | 6/2011  | Oyler | 435/134 |

FOREIGN PATENT DOCUMENTS

| CN | 1858215 A |   | 11/2006 |         |
|----|-----------|---|---------|---------|
| JP | 52082785 A | * | 7/1977 |          |
| JP | 60105484 A | * | 6/1985 |          |
| JP | 61108365 A | * | 5/1986 |          |
| JP | 07-031485 |   | 2/1995 |           |
| JP | 2002-265962 |  | 9/2002 |          |
| JP | 2003-310288 |  | 11/2003 |         |
| KR | 1020060068075 A | | 6/2006 |        |
| WO | WO 9637627 A1 | * | 11/1996 | C12P 7/10 |

OTHER PUBLICATIONS

Olaitan, S. and Northcote, D. "Polysaccharides of *Chlorella pyrenoidosa*" Biochemical Journal (1962) vol. 82, 509-519.*

Armisen, R. and Galatas, F. "Chapter 1—Production, Properties and uses of Agar" Production and utilization of products from commercial seaweeds. Edited by Dennis J. McHugh, FAO Fisheries Technical Paper 288, (1987) Food and Agriculture Organization of the United Nations. ISBN 92-5-102612. pp. 1-29 of chapter 1.*

Katou et al ("Brewing characteristics of haplois strains isolated from sake yeast Kyokai No. 7", Yeast, 2008, vol. 25, 799-807).*

Miller et al ("The structure of the galactan from *Aeodes nitidissima* (Halymeniales, Rhodophyta)" Botanica Marina 48 (2005) 137-142).*

Denis et al ("Effect of enzymatic digestion on thallus degradation and extraction of hydrosoluble compounds from *Grateloupia turuturu*" Botanica Marina 52 (2009) 262-267).*

El-Sayed et al Abstract-"Purification and characterization of agar from *Digenea simplex*" Carbohydrate Research vol. 118, 1983, 119-126.*

Turvey et al "The Hydrolysis of Algal Galactans by Enzymes from a *Cytophaga* Species", Biochemical Journal, 1967, 105 311-317.*

JP61-108365, Derwent Abstract and Partial Translation.*

JP-60105484, Derwent Abstract and Partial translation provided).*

(Continued)

*Primary Examiner* — Jon P Weber
*Assistant Examiner* — Charles Zoltan Constantine
(74) *Attorney, Agent, or Firm* — Cooley LLP

(57) ABSTRACT

The present invention relates to a method of producing biofuel, more specifically a method of producing biofuel comprising the steps of generating monosugars from marine algae, or from polysaccharides extracted from marine algae by treating the marine algae or the polysaccharides with a hydrolytic enzyme and/or a hydrolytic catalyst; and fermenting the monosugars using a microorganism to produce biofuel. The method of producing biofuel of the present invention solve the problem of raw material suppliance since it uses marine algae as a raw material for biomass, and reduce the production costs by excluding lignin eliminating process that has been required by the conventional method using wood-based raw materials, resulting in economic and environmental advantages.

9 Claims, 15 Drawing Sheets

(56) References Cited

OTHER PUBLICATIONS

Gough "Continuous ethanol production from molasses at 45 °C using alginate-immobilized *Kluyveromyces marxianus* IMB3 in a continuous-flow bioreactor" Bioprocess Engineering 19, 1998, 33-36.*

Pilar Ruperez et al., "Potential Antioxidant Capacity of Sulfated Polysaccharides from the Edible Marine Brown Seaweed *Fucus vesiculosus*", J. Agric. Food Chem. 2002 vol. 50. pp. 840-845.

Henry R . Bungay, "Confessions of a Bioenergy Advocate", Trends in Biotechnology, 2004, vol. 22. No. 2. pp. 67-71.

Mee-Ok Yoon et al., "Comparison of Alginic Acid Yields . . .", J. Korean Soc. Food Sci. Nutr. (2004) vol. 33. pp. 747-752.

"Supplementary European Search Report," 8 pages, EP appl. No. 08723140.3 (Aug. 29, 2013).

Pakulski and Benner, "An improved method for the hydrolysis and MBTH analysis of dissolved and particulate carbohydrates in seawater," Marine Chem. 40:143-160 (1992).

Matsumoto, M., et al., Saccharification of Marine Microalgae Using Marine Bacteria for Ethanol Production; Applied Biochemistry and Biotechnology; vol. 105-108, 2003; pp. 247-254.

Yoon, M-O, et al., Comparison of Alginic Acid Yields and Viscosity by Different Extraction Condition from Various Seaweeds; J Korean Soc Food Sci Nutr, 33(4), 747-752 (2004.).

Written Opinion and International Search Report for PCT/KR2008/001102; dated Jun. 9, 2008;10 pages.

International Preliminary Report on Patentability for PCT/KR2008/001102, dated Jun. 9, 2009; 5 pages.

English Translation of the 4th Office Action recieved from the State Intellectual Property Office of the People's Republich of China for Application No. 200880010031.8.

* cited by examiner

METHOD OF PRODUCING BIOFUEL USING SEA ALGAE

FIELD OF THE INVENTION

The present invention relates to a method of producing biofuel, more precisely a method of producing biofuel using marine algae.

DESCRIPTION OF THE RELATED ART

Biofuel is generally defined as energy obtained from biomass, through direct combustion, alcohol fermentation, and methane fermentation, etc. Biomass, the raw material of biofuel, especially for bioalcohol, can be classified into sugar-based (sugarcane, sugarbeet, etc), starch-based (corn, potato, sweet potato, etc) and wood-based (wastewood, rice straw, wastepaper, etc). The sugar-based biomass can be easily and directly converted into bioethanol by fermentation after comparatively simple pretreatment process. Whereas the starch- or wood-based biomass requires proper pretreatment process and saccharification process to produce bioethanol. The waste wood, a sort of municipal waste, or forest by-product scattered around forest can also be used as as wood-based biomass. Furthermore, since they have no usability as food, the raw material suppliance can be stably secured. However, for wood-based biomass to be used as biofuel, a pretreatment of lignin elimination has to be carried out, which increases production costs, and the saccharification efficiency becomes very low due to the crystalline hydrogen bonded structure of cellulose.

For an alternative fuel to be economically viable for transportation, the price of biofuel must be competitive with gasoline. In general, the cost ratio of raw material to processing is largely dependent on the types of biomass used. For example, in the case of sugar-based such as sugarcane and sugarbeet, the cost ratio of raw material to processing is approximately 75:25. In the meantime, in the case of starch-based such as corn, potato, and cassava, the ratio is about 50:50 and in the case of wood-based, the ratio is approximately 25:75.

The most commonly used biomass for the production of bioethanol until now has been sugar-based and starch-based. However, they also can be utilized as food, therefore, these raw material suppliances should be influenced if the food demands rapidly increase, resulting that the production cost would not be economically feasible. Furthermore, the cultivation of crops such as corns was found to require huge amount of agricultural chemicals and nitrogenous fertilizers, resulting in environmental problem such as soil erosion and contaminations.

The worldwide bioethanol production reached approximately 51.3 billion liters as of 2006. The production of biofuel using sugar-based, specifically bioethanol, is approximately 18.7 billion liters (as of 2006) and major production countries are Brazil, India, and Taiwan, in particular Brazil leads the production (17.8 billion liters) (Global Bioenergy Partnership (GBEP), 2006). Brazil actively produces bioethanol for transportation using sugarcane as a raw material which is abundant, and thereby various types of bioethanol mixed gasoline called gasohol are provided. In 2003, FFV (Flexible Fuel Vehicle) that is operable with variable bioethanol/gasoline ratio was started to be sold and as of May, 2005, FFV sale took approximately 50% of the total vehicle sale.

The world wide production of bioethanol using corn is approximately 19.8 billion liters (as of 2006). And major producing countries are U.S., Europe and China, and in particular U.S. is the leading country who produces 18.5 billion liters of bioethanol (see Table 1). U.S. enacted Energy Tax Act in 1978 right after oil shock hit the Country, which is to increase the supply of such gasoline that contains bioethanol up to 10% by reducing federal tax by 4$ per gallon. U.S. produces actively bioethanol by taking advantage of wide arable land and abundant raw material, corn, as an effort of new & renewable development facilitating breaking from the dependence on petroleum. Effort for bioethanol production as an alternative energy has been one of the main strategies in U.S., especially, the development of corn-based bioethanol production policy is getting stronger and wider.

There is no predictable industrial trend in producing biofuel using wood-based biomass because it is still far from commercialization. But, Iogen in Canada has been actively developing technology to produce biofuel using wood-based biomass and U.S. government will keep increasing funds of 1.5 billion dollars from the budget for 2007 for the utilization of the technique facilitating the production of bioethanol using next generation biomass such as agricultural waste and lignocellulosic materials till 2012, in order to be able to substitute 30% of the total transportation fuel with bioethanol.

TABLE 1

Comparison of economic values of bioethanol according to raw materials) (originated from DOE, EPA, Worldwatch Institute)

|  | Corn-based ethanol | Sugar-based ethanol | Lignocellulosic ethanol |
|---|---|---|---|
| Worldwide production(l) | 19.8 billion (2006) | 18.7 billion (2006) | 0 |
| Production per unit area (l/ha) | 2,500 | 5,700-7,600 | 5,500 (switchgrass) |
| Production cost ($/l)(2007) | 0.29-0.33 | 0.19-0.23 | R&D stage |
| Retail price ($/l) | Gasoline: 0.80 E85: 0.69 E85: 0.98[1] | E25: 1.30 E100: 0.77 E100: 1.03 | R&D stage |
| Energy balance[2] | 1:1.3 | 1:8 | 1:2-36 (deviation from production method) |
| Greenhouse gas emission (g/l) (gasoline: 2437.8) | 1935.9 (22% reduction) | 1075.5 (56% reduction) | 227.05 (91% reduction) |

[1] Cost for energe corresponding to 1 liter of gasoline
[2] Biofuel yield compared to supplied fossile fuel used for biofuel production Meanwhile, marine algae are classified into macroalgae and microalgae. Macroalgae include red algae, brown algae, and green algae, while microalgae include *chlorella* and spirulina, etc. The world wide annual marine algae production is approximately 14 million tons and is expected to increase more than 22 million tons in 2020. This production corresponds to about 23% of the total production from marine cultivation. Particularly, brown algae such as sea mustard and marine tangle and red algae such as layer, *Gelidium amansii*, and sea string take at least 90% of the total marine algae production. The amount of marine algae production in Korea reaches approximately 500,000 tons/year as of today, which is slightly reduced in the mid-90s (approximately 700,000 tons) but the total area of farms increased from 60,000 ha in the mid-90s to 70,000 ha.

Compared with other type of land biomass, marine algae are growing very fast (4-6 times of harvest/year is possible in subtropic region) and easy to cultivate using wide arable area of the ocean without using high priced materials such as irrigation water, land, fertilizer, etc. Utilization of marine algae takes advantages of simple production processes for biofuel because it does not contain lignin that has to be eliminated. In addition, the amount of annual $CO_2$ absorption ability of marine algae is 36.7 tons per ha, which is 5-7 times higher than that of wood-based. Therefore, if E20 (gasoline containing bioethanol by 20%) is used, the annual greenhouse gas reduction rate will be approximately 27%, which will reduce carbon tax approximately 300 billion Korean Wons, if converted into money value (Table 2).

TABLE 2

Charactistics of land plant and marine plant

| | Land plant | | Maritime plant |
|---|---|---|---|
| | Sugar- and starch-based (1st generation) | Wood-based (2nd generation) | Marine algae (3rd generation) |
| Raw material | Sugarcane, corn | wood | Gelidium amansii, Gracilaria, Cottonii |
| Harvest interval | 1-2 times/year | At least 8 years | 4-6 times/year |
| Yield/unit area (tons/ha) | 180 | 9 | 565 |
| $CO_2$ absorption/ unit area (tons/ha) | 5-10 | 4.6 | 36.7 |
| Production process | Simple | Complex (lignin elimination) | Simple (lignin absent) |
| Cultivation environment | Sunlight, $CO_2$, irrigation water, soil, fertilizer | Sunlight, $CO_2$, irrigation water, soil, fertilizer | Sunlight, $CO_2$, marinewater |

Because marine algae have been largely applied in fine chemical and medical materials such as electrophoresis reagent, fertilizer, emulsifier, anticancer agent, etc, or in health food as either food or medicine, there have been no reports or studies on the development of marine algae as biomass for biofuel production until now.

SUMMARY OF THE INVENTION

The present invention is designed and applied in order to overcome the problems of the conventional biofuel production method. Precisely, it is an object of the present invention to provide a method of producing biofuel using marine biomass as a new raw material to solve the problems of instability/unbalance of demand and supply of raw material and low saccharification efficiency by using marine algae instead of the conventional biomass such as sugar-, starch- or wood-based materials.

DETAILED DESCRIPTION OF THE PREFERRED EMBODIMENTS

The method of producing biofuel using marine algae of the present invention comprises the steps of generating monosugars by treating marine algae or polysaccharides extracted from marine algae with a hydrolytic enzyme and/or a hydrolytic catalyst; and fermenting the monosugars by using a microorganism.

In the present invention, the biofuel includes $C_1$-$C_4$ alcohol or $C_2$-$C_4$ ketone, and preferably methanol, ethanol, propanol, butanol or acetone, but not limited thereto. The polysaccharides herein include agar, starch, cellulose, carrageenan, alginic acid, etc, but not limited thereto.

Marine algae used in the method of producing biofuel of the present invention are not limited and any algae selected from macroalgae or microalgae can be used. The macroalgae include red algae, brown algae, and green algae, while the microalgae include *chlorella* and spirulina, etc. Red algae are exemplified by *Gelidium amansii*, laver, *Cottonii*, *Grateloupia lanceolata*, *Porphyra suborbiculata*, *Pterocladia tenuis*, *Acanthopeltis japonica*, *Gloiopeltis tenax*, *Gracilaria verrucosa*, *Chondrus ocelatus*, *Pachymeniopsis elliptica*, *Hypnea charoides*, *Ceramium kondoi*, *Ceramium boydenii*, *Gigartina tenella*, *Campylaephora hypnaeoides*, *Grateloupia filicina*, etc, but not limited thereto. Among these, *Gelidium amansii* is preferred. Among red algae, *Gelidium amansii* has the widest variety and exhibits high growth rate. It contains cellulose, approximately 15-25% and agar, which is composed mostly of galactan, approximately 50-70%, and additionally protein less than 15% and lipid less than 7% based on the total dry weight. Brown algae are exemplified by *Undaria pinnatifida*, *Laminaria japonica*, *Analipus japonicus*, *Chordaria flagelliformis*, *Ishige okamurai*, *Scytosiphon lomentaria*, *Endarachne binghamiae*, *Ecklonia cava*, *Ecklonia stolonifera*, *Eisenia bicyclis*, *Costaria costata*, *Sargassum fulvellum*, *Sargassum horneri*, *Sargassum thunbergii*, *Hitzikia fusiformis*, etc, but not limited thereto. Brown algae are multicellular organisms and well differentiated in algae family. Green algae are exemplified by *Ulva lactuca*, *Spirogyra* spp., *Enteromorpha*, *Codium fragile*, *Codium minus*, *Caulerpa okamurai*, *Nostoc commune*, etc, but not limited thereto. Green algae have chlorophyll, so that they produce starch-based by photosynthesis. As for components of brown algae and green algae, brown algae contain alginic acid approximately 30-40% and cellulose 5-6%, while green algae contain starches, approximately 40-50% and cellulose less than 5%.

Agar contains galactan composed of galactose polymer as a major component. Galactan can be converted into monosugars such as galactose and 3,6-anhydrogalactose by proper depolymerization. Cellulose takes approximately 15-25% of the total components of *Gelidium amansii*. The cellulose is converted into glucose, a monosugars, by saccharification using a proper enzyme or an acid catalyst. The galactose and glucose can be used for substrate of biofuel which can be converted into biofuel by fermentation.

Starch is generally called dextrin, which is a carbohydrate synthesized in chloroplast of plants by photosynthesis and stored therein. The starch is a polysaccharide composed of glucose, which can be converted into glucose, a monosaccharide, by saccharification using a proper enzyme or an acid catalyst.

A method for extracting polysaccharides such as agar, cellulose, starch, carrageenan, alginic acid, etc, from marine algae is not limited and any method known to those skilled in the art can be accepted. In a preferred embodiment of the present invention, marine algae are dipped in alkali aqueous solution for a while, washed with water, and then soaked in an extracting buffer comprising acidic reagent, followed by extraction of agar, carrageenan, and alginic acid therefrom. Then, remaining cellulose and starch are collected. The extraction temperature is not limited, but 80-150° C. is preferred. The acidic reagent used herein is selected from the group consisting of $H_2SO_4$, HCl, HBr, $HNO_3$, $CH_3COOH$, HCOOH, $HClO_4$ (perchloric acid), $H_3PO_4$ (phosphoric acid), PTSA (para-toluene sulfonic acid) and commonly used solid acid, but not limited thereto. The alkali aqueous solution is selected from the group consisting of potassium hydroxide, sodium hydroxide, calcium hydroxide and ammonia aqueous solution, but not limited thereto.

Monosugars can be obtained by saccharification of polysaccharides such as agar, starch, cellulose, carrageenan and alginic acid by treating such polysaccharides with a proper hydrolytic enzyme and/or a hydrolytic catalyst. The monosugars herein are galactose, 3,6-anhydrogalactose, glucose, fucose, rhamnose, xylose and mannose, etc, but not limited thereto.

The saccharification process herein can be either direct saccharification or indirect saccharification. Hereinafter, these two saccharification methods and the method of fermentation for biofuel using the hydrolyzate obtained thereby are described in detail.

First is an example of indirect saccharification which uses agar as a starting material. Agar contains galactan, galactose polymer, as a major component. Galactan is converted into monosugars such as galactose and 3,6-anhydrogalactose, which can be fermented by proper fermentation process. At this time, a method for saccharification is acid-hydrolysis or enzymatic hydrolysis. Acid-hydrolysis is a method converting galactan into low molecules using an acid hydrolytic catalyst. The catalyst herein can be selected from the group consisting of $H_2SO_4$, HCl, HBr, $HNO_3$, $CH_3COOH$, HCOOH, $HClO_4$, $H_3PO_4$, PTSA and commonly used solid acid. The concentration of the acid used and the temperature and reaction time can be regulated to maximize production efficiency of galactose and at this time it is preferred not to over-hydrolyze galactose newly generated. The method for saccharification of agar using an enzyme could not be as efficient as acid-hydrolysis, but once an optimum galactosidase group is selected, the conversion yield can be improved. The enzyme that is able to hydrolyze galactan is β-agarase or β-galactosidase, but not limited thereto. The β-agarase can be obtained from *Pseudomonas atlantica* or *E. coli*, while the β-galactosidase can be obtained from *Aspergillus oryzae* or Bovine testes. In a preferred embodiment of the present invention, monosaccharides are obtained from agar by hydrolysis performed at 60-200° C. for 0-6 hours using a hydrolytic catalyst such as $H_2SO_4$, HCl, HBr, $HNO_3$, $CH_3COOH$, HCOOH, $HClO_4$, $H_3PO_4$ or PTSA of the concentration of 0.05-30% for the agar.

Here is another indirect saccharification which uses cellulose as a stating material. Cellulose can be converted into glucose by hydrolysis using a hydrolytic enzyme and/or an acid hydrolytic catalyst. Approximately 52 different commercialized enzymes for hydrolyzing cellulose are known and among these commercialized β-glucosidase (production strain: *Thermotoga maritima*) and endo-1,4-β-glucanase (production strain: *Aspergillus niger, Trichoderma longibrachiatum, Talaromyces emersonii, Trichoderma reesei* and *Trichoderma viride*) are preferred, but not limited thereto. The catalyst herein can be selected from the group consisting of $H_2SO_4$, HCl, HBr, $HNO_3$, $CH_3COOH$, HCOOH, $HClO_4$, $H_3PO_4$, PTSA and commonly used solid acid. The concentration of the acid used and the temperature and reaction time can be regulated to maximize production efficiency of glucose and at this time it is preferred not to over-hydrolyze glucose newly generated. In a preferred embodiment of the present invention, monosaccharides are obtained from cellulose by hydrolysis performed at 80-300° C. for 0-6 hours using a hydrolytic catalyst such as $H_2SO_4$, HCl, HBr, $HNO_3$, $CH_3COOH$, HCOOH, $HClO_4$, $H_3PO_4$ or PTSA at the concentration of 0.05-50% for the cellulose. In another preferred embodiment of the present invention, monosaccharides are obtained from cellulose by a hydrolytic enzyme-mediated reaction for 0-144 hours.

Another example of indirect saccharification is the one that uses starch as a starting material. Starch is composed of glucose, so it can be easily converted into glucose by hydrolysis using a hydrolytic enzyme and/or an acid hydrolytic catalyst. The commercial enzyme hydrolyzing starch is exemplified by amylase, but not limited thereto. Amylase is an enzyme hydrolyzing polysaccharides, which is mainly working on such polysaccharides that are composed of α-linked glucose such as dextrin (amylose and amylopectin) or glycogen. According to working mechanism, the enzyme is classified into three categories such as α-amylase, β-amylase and glucoamylase. The microorganisms that can produce amylase are exemplified by *Aspergillus oryzae, Aspergillus niger, Rhizopus oryzae, Saccharomyces cerevisiae, Bacillus subtilis, Bacillus licheniformis, Streptomyces griseus* or *Pyrococcus furiosus*, but not limited thereto. The catalyst that is able to hydrolyze starch can be selected from the group consisting of $H_2SO_4$, HCl, HBr, $HNO_3$, $CH_3COOH$, HCOOH, $HClO_4$, $H_3PO_4$, PTSA and commonly used solid acid. The concentration of the acid used and the temperature and reaction time can be regulated to maximize production efficiency of glucose and at this time it is preferred not to over-hydrolyze glucose newly generated.

In the meantime, direct saccharification includes the procedure to hydrolyze the materials directly from marine algae containing cellulose and/or agar and carrageenan or marine algae containing starch and/or alginic acid and cellulose as a starting material. At this time, enzymatic hydrolysis or acid-hydrolysis can be used. For enzymatic hydrolysis, it can be important to select proper enzyme for efficient hydrolysis because the major substrates of marine algae are galactan and cellulose; or carrageenan and cellulose; or alginic acid and cellulose; or starch and cellulose, and that of the enzyme to convert the components into glucose might be different from the mechanism of the enzyme to convert the materials into galactose and 3,6-anhydrogalactose. Two or more enzymes can be used simultaneously. For example, green algae contain two different polysaccharides such as starch and cellulose, so that the enzyme group comprising an enzyme capable of hydrolyzing starch and another enzyme capable of hydrolyzing cellulose can be preferably used. For acid-hydrolysis, the acid hydrolytic catalyst is not limited and any hydrolytic catalyst used in indirect saccharification as mentioned above can be used. The concentration of the acid catalyst used and the temperature and reaction time can be regulated to maximize production efficiency of glucose and galactose and at this time it is important not to over-hydrolyze monosaccharides newly generated. For the saccharification using original marine algae as a starting material, it is preferable to wash the marine algae to eliminate impurities and then completely dried by hot air or natural air drying. The dried marine algae are pulverized by using raw mill to give fine powders. In a preferred embodiment of the present invention, the monosaccharides are obtained from the original marine algae by hydrolysis performed at 60-300° C. for 0-6 hours using a hydrolytic catalyst such as $H_2SO_4$, HCl, HBr, $HNO_3$, $CH_3COOH$, HCOOH, $HClO_4$, $H_3PO_4$ or PTSA at the concentration of 0.05-50% for the marine algae. In another preferred embodiment of the present invention, the monosaccharides are obtained from the original marine algae by multi-step saccharification in which the first saccharification is performed at 60-300° C. for 0-6 hours using a hydrolytic catalyst selected from the group consisting of $H_2SO_4$, HCl, HBr, $HNO_3$, $CH_3COOH$, HCOOH, $HClO_4$, $H_3PO_4$, PTSA and commonly used solid acid of the concentration of 0.05-50% for the marine algae and then the second and the third saccharifications are performed with the remaining cellulose or starch under the same conditions as above.

The hydrolyzate containing the generated galactose, 3,6-anhydrogalactose, glucose or their sugar mixtures can be converted into bio-alcohol using a microorganism for biofuel fermentation such as yeast. The yeasts for fermentation which can be used in the present invention are *Clostridium acetobutylicum*, *Clostridium beijerinckii*, *Clostriduim aurantibutylicum* and *Clostridium tetanomorphum*, etc, but not limited thereto, and they are particularly preferred for butanol or acetone fermentation. The yeast such as *Saccharomyces cerevisiae*, *Sarcina ventriculi*, *Kluyveromyces fragilis*, *Zymgomomonas mobilis*, *Kluyveromyces marxianus* IMB3 and *Brettanomyces custersii*, etc, can also be used, and these yeasts are particularly preferred for ethanol fermentation.

Biobutanol, among many biofuels, has similar characteristics to gasoline, which satisfies energy density, volatility, high octane number, and low impurity rate, etc. Mixed fuel containing bio-butanol by about 10% demonstrates similar capacity with gasoline. And, energy density of bio-butanol almost approaches to that of unleaded gasoline. Unlike bio-ethanol, bio-butanol is not phase-separated even in the presence of water and has low oxygen content, affording high concentration of bio-butanol mixture, which facilitates the combination of high concentration of bio-butanol with gasoline.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

In the present invention, experiments were performed using the saccharification apparatus, materials and analysis methods as follows.

1. Saccharification Apparatus

Figure 1:
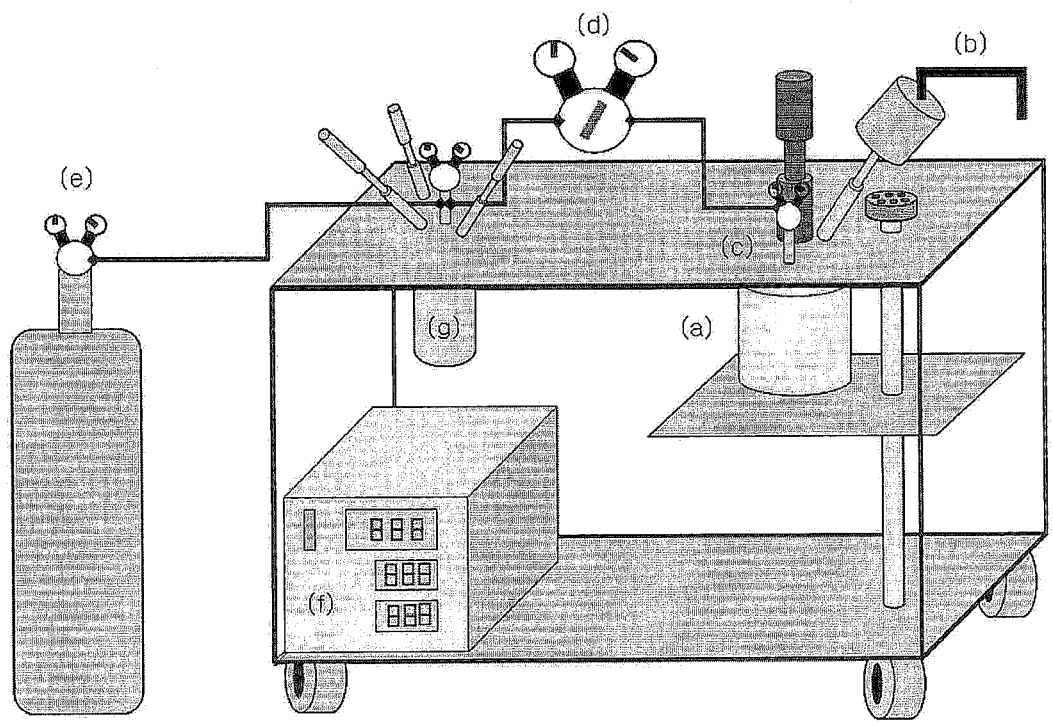
FIG. 1 is a schematic diagram of hydrolysis apparatus. (a) batch reactor, (b) sampling port, (c) pressure gauge, (d) $N_2$ gas regulator, (e) $N_2$ gas bombe, (f) control box, (g) $N_2$ gas reservoir.

The saccharification system equipped with a reactor and a control box used for saccharification experiment is described in FIG. 1. The reactor was designed as a sylindral reactor having 500 ml of volume (effective volume: 400 ml) and has inside height of 12.5 cm and inside diameter of 7 cm. Temperature jacket was attached thereto to regulate reaction temperature to the designated temperature. Thermocouple was equipped thereto to measure the inside temperature of the reactor. To prevent over-heating, cooling water was designed to circulate outside of the reactor. To make the sampling easy during the reaction, high pressure $N_2$ gas was made to be injected from the outside of the reactor, for which $N_2$ gas tank and sample port were equipped thereto. The control box, in the meantime, was equipped with a RPM meter, a digital temperature regulator, and a pressure gauge.

2. Materials 2.1. Substrates

In the examples, *Gelidium amansii* from Morocco, *Gelidium amansii* from Jeju island, Korea, marine string and *Cottonii* were used as red algae, and *Codium fragile* was used as green algae. In addition, marine tangle was used as brown algae.

In the examples, experiments were carried out by two different methods; one is direct saccharification using

*Gelidium amansii* as a raw material and the other is indirect saccharification using cellulose and agar separated/extracted from *Gelidium amansii* as a raw material. For the direct saccharification, *Gelidium amansii* was washed with distilled water, dried at 40° C., followed by pulverization and filtered with 106 or 300 mesh. For the indirect saccharification, agar was extracted from *Gelidium amansii* which was soaked in KOH aqueous solution for a while and washed with distilled water, followed by extraction of agar using distilled water or ethyl alcohol or methyl alcohol, dried at 40° C. and pulverized. After extraction of agar, the remaining cellulose was bleached with $O_3$ twice (1 h/1 bleach) and then bleached again with $ClOC_2$ at 60° C. twice (1.5 h/1 bleach) and then bleached again with $H_2O_2$ at 80° C. twice (1 h/1 bleach) to give separated cellulose.

2.2. Strains and Medium

In the examples, *Saccharomyces cerevisiae* DKIC413 and *Brettanomyces custersii* H1-39 (Korean Culture Center of Microorganisms, KCCM 11490) were used and YEPD (yeast extract 10 g/l, peptone 20 g/l, dextrose 20 g/l) was selected as a culture medium. The medium was sterilized in autoclave (Woosung Scientific Co., Korea) at 121° C. for 15 minutes.

2.3. Enzymes

The enzymes used in the examples are commercially available and purchased from Biosys Co., Korea. Celluclast prepared by concentrating *Trichoderma reesei* culture solution is a kind of cellulase hydrolyzing cellulose into glucose and cellobiose. Viscozyme prepared by concentrating *Aspergillus aculeatus* culture solution is an enzyme complex comprising cellulase, β-glucanase, hemicellulase and xylanase. Spirizyme and AMG (Amylo Glucosidase) are amyloglucosidases produced from *Aspergillus niger*, which are enzymes hydrolyzing malto-oligomer converted from starch into glucose by α-amylase and isoamylase. Lactozyme prepared by concentrating *Kluyveromyces fragilis* culture solution is a kind of lactase hydrolyzing lactose into glucose and galactose. Functions of each enzyme and conditions for hydrolysis are shown in Table 3.

3. Method for Analysis 3.1. Sugar Analysis

Hydrolyzate was analyzed with HPLC (ICS-3000, Dionex Co., USA) equipped with current detector. At this time, Carbopac PA 1 (4250 mm, Dionex Co., USA) and Carbopac PA 1 (450 mm, Dionex Co., USA) were used as columns. As a moving phase, 16 mM NaOH solution was used. Flow rate was 1 ml/min, and column temperature was 30° C. The concentrations of glucose and galactose were quantified by using correction curve of a standard material. The yields of glucose and galactose were calculated according to formula 1, indicating the ratio of the generated glucose and galactose to the total dried weight of the raw material.

$$\text{Yield (\%)} = C \times V/S \times 100 \quad \text{[Formula 1]}$$

C=concentration of glucose or galactose (g/l)
V=total amount of solvent used for saccharification (l)
S=total amount of substrate (protein, cellulose, galactan, others) used for saccharification (g)

3.2. Protein Analysis (Semi-Micro Kjeldahl Method)

To analyze protein sample, 0.5 g of the protein sample was put in a protein decomposition tube, to which 20 ml of sulfuric acid and 5 g of proteolysis promoter ($K_2SO_4$: $CuSO_4.5H_2O$=9:1) were added, followed by decomposition of the protein. Upon completion of the decomposition, 70 ml of distilled water was added thereto. 75 ml, of 32% NaOH was added to the distiller, followed by distillation using protein distillation apparatus. Ammonia generated by the distillation was collected with 100 ml of 3% boric acid and titrated with 0.1 N HCl. Total nitrogen content was calculated by formula 2.

$$\text{Protein amount (\%)} = 0.0014 \times (V_1 - V_0) \times f \times N/S \times 100 \quad \text{[Formula 2]}$$

$V_0$=0.1 N HCl consumption of blank sample (ml)
$V_1$=0.1 N HCl consumption of sample (ml)
f=0.1 N HCl factor
N=nitrogen coefficient
s=sample amount (mg)
0.0014: nitrogen amount corresponding to 1 ml of 0.1 N HCl (g)

3.3. Ash Analysis (Dry Ashing Method)

A crucible was heated in a 550° C. furnace until it reached constant weight, followed by cooling in a desiccator and measuring. 2 g of sample was put in the measured crucible, followed by ashing in a 550° C. furnace until it turned into white or gray ashes. The ashes were cooled down in the furnace at 200° C., and then transferred into a desiccator, followed by cooling down again at room temperature. Ash content (%) was calculated by formula 3.

$$\text{Ash (\%)} = (W_0 - W_1)/S \times 100 \quad \text{[Formula 3]}$$

$W_1$=constant weight of crucible (g)
$W_0$=weight of crucible after ashing+ash (g)
S=sample weight (g)

TABLE 3

Enzyme property and hydrolysis conditions

| Enzyme | Properties | Hydrolysis conditions | Activity | Purpose |
|---|---|---|---|---|
| Celluclast | Cellulose hydrolysis | pH: 4.5-6.0, Temp.: 50-60° C. | 700 EGU[1]/g | Cellulose hydrolysis |
| Viscozyme | Cellulose, xylose, hemicellulose hydrolysis | pH: 3.3-5.5, Temp.: 25-55° C. | 100 FBG[2]/g | Agar hydrolysis |
| Spirizyme | Starch, maltose hydrolysis | pH: 4.2-4.5, Temp.: 60-63° C. | 400 AG[3]/g | Agar hydrolysis |
| AMG | Starch, maltose hydrolysis | pH: 4.5, Temp.: 60° C. | 300 AG/g | Agar hydrolysis |
| Lactozym | Lactose hydrolysis | pH: 6.5, Temp.: 37° C. | 3000 LAU[4]/ml | Agar hydrolysis |

[1]EGU: endo-glucanase unit
[2]FBG: fungal glucanase unit
[3]AG: 1 μmol maltose/min
[4]LAU: 1 mmol glucose/min 3.4. Measurement of Cell Concentration The cell concentration was measured by using a spectrophotometer (Genesys 10-S, Thermo electron corp., USA) at 600 nm. The sampling of culture solutions were performed over the time, followed by centrifugation using a centrifuge (VS-150FN, Vision Science Co., LTD., Korea) at 3,500 rpm for 10 minutes. The precipitate was washed with distilled water and centrifuged again. The precipitate was dried at 50° C. for 24 hours, followed by measuring the weight of dried sample. The dry cell weight of *Saccharomyces cerevisiae* was calculated by the following formula: Dry cell weight=0.3135 OD+0.1811 (correlation coefficient=0.994), while the dry cell weight of *Brettanomyces custersii* was calculated by the following formula: Dry cell weight=0.1292 OD+0.8554 (correlation coefficient=0.999).

3.5. Ethanol Analysis.

Ethanol concentration in the fermentation culture solution was measured by HPLC (Breeze HPLC system, Waters Co., USA) equipped with RI detector. At this time, Aminex HPX-87H (300 7.8 mm, Bio-rad) was used as a column. 5 mM of sulfuric acid aqueous solution was used as a moving phase and the flow rate was 0.6 ml/min and the temperature of the column and RI detector was set at 50° C. The ethanol content was quantified by using correction curve of a standard material.

Example 1

Analysis of Compositions of Cellulose and Galactan in Different Marine Algae 0.3 g of marine algae (*Gelidium amansii* from Morocco, *Gelidium amansii* from Jeju island, marine string, Cottonii, *Codium fragile*, marine mustard or marine tangle) and 3 ml of 72% sulfuric acid aqueous solution were added into a glass tube, followed by reaction at 30° C. for 2 hours (the first hydrolysis). Upon completion of the reaction, the reaction mixture was put in a 250 ml bottle, to which 84 ml of distilled water was added, followed by hydrolysis in an autoclave (VS-150FN, Vision Science Co., LTD., Korea) at 121° C. for 1 hour (the second hydrolysis). Upon completion of the second hydrolysis, the bottle was taken out when the inside temperature was 50° C. and then cooled down to room temperature. 1 ml of the reaction mixture was taken from the bottle and neutralized with $CaCO_3$, followed by centrifugation using a centrifuge (VS-150FN, Vision Science Co., LTD., Korea) at 8,000 rpm for 10 minutes to eliminate $CaSO_4$. The compositions of cellulose and galactan were calculated.

As shown in Table 4, despite they were the same species of marine algae, the compositions were found to be different according to the growing locations. Precisely, the carbohydrate content was highest in *Gelidium amansii* (from Morocco or Jeju island, Korea), which was 70-80%, and lowest in marine mustard (40%). The content of non-carbohydrate (protein, lipid and others) was highest in marine mustard (59%) and lowest in *Gelidium amansii* (from Morocco or Jeju island, Korea), which was 20-28%, suggesting that *Gelidium amansii*, one of red algae, has a highest potential as a good raw material for ethanol production. Thus, after this experiment, *Gelidium amansii* from Morocco having comparatively high carbohydrate content was selected as a substrate for saccharification/fermentation.

TABLE 4

Chemical composition of marine algae

| | marine algae | Cellulose (%) | Galactan (%) | (Carbohydrate) (%) | Protein (%) | Etc. (lipid, ash) (%) |
|---|---|---|---|---|---|---|
| Red algae | *Gelidium amansii*, Morocco | 16.8 | 55.2 (Gal: 28%, AHG: 27%) | 72.0 | 21.1 | 6.9 |
| | *Gelidium amansii*, Jeju | 23.0 | 56.4 | 79.4 | 11.8 | 8.8 |
| | *Gracilaria* | 19.7 | 54.4 | 74.1 | 11.0 | 14.9 |
| | Cottonii | 7.1 | 43.4 | 50.5 | 4.9 | 44.6 |
| Green Algae | *Codium fragile* | 10.9 | 47.8 | 58.7 | 34.7 | 6.6 |
| Brown algae | *Undaria pinnattnda* | 2.4 | 38.7 | 41.1 | 24.2 | 34.7 |
| | *Laminaria japonica* | 6.7 | 40.0 | 46.7 | 12.2 | 38.1 |

Example 2

Saccharification Experiment

<2-1> Saccharification by Acid-Hydrolysis 75 g of the substrate and 1% sulfuric acid aqueous solution were added into a 4 l Erlenmeyer flask, followed by reaction at 121° C. for 15 minutes. Then, the temperature was lowered to room temperature and the hydrolyzate was neutralized with $CaCO_3$. In a separated experiment, centrifugation was performed using a centrifuge (VS-150FN, Vision Science Co., LTD., Korea) at 8,000 rpm for 10 minutes to eliminate $CaSO_4$. The substrate (5.5-15.0%) and sulfuric acid aqueous solution (0.5-4.0%) were added into a high pressure reactor according to S/L ratio, followed by saccharification at the designated temperature (80-200° C.) for required time (0-4 hours). Samples were taken for analysis at every time specified and upon completion of the reaction, the temperature of the reactor was lowered to room temperature, followed by sampling for analysis. All of the samples were neutralized with $CaCO_3$, followed by centrifugation to remove $CaSO_4$. The centrifugation was performed using a centrifuge (VS-150FN, Vision Science Co., LTD., Korea) at 8,000 rpm for 10 minutes. The results are as follows.

<2-1-1> Saccharification Using Agar (*Gelidium Amansii*)

Figure 2:
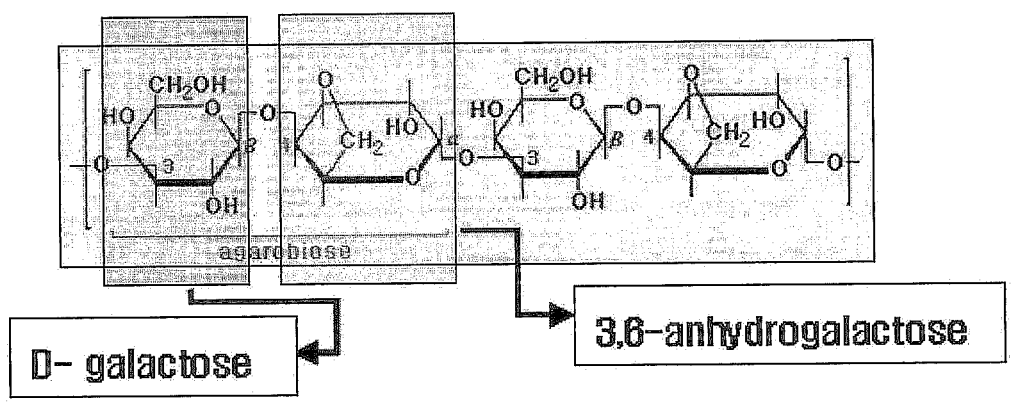
FIG. 2 is a chemical formula showing the binding structure of agarose.
Figure 3:
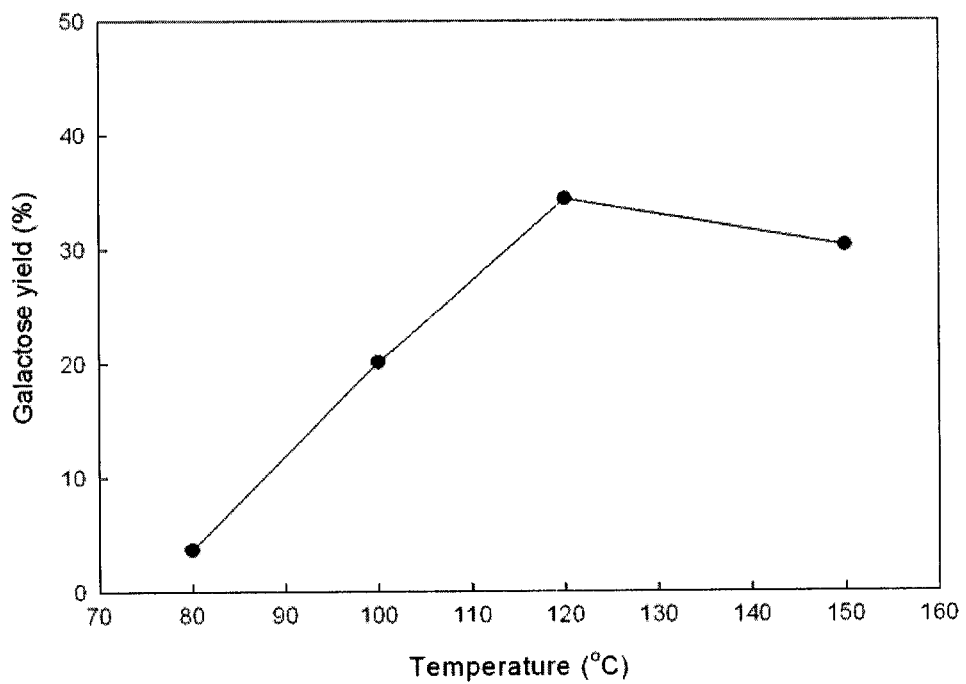
FIG. 3 is a graph showing the effects of reaction temperatures on the galactose yields using agar as a substrate. Experimental conditions: substrate 10 g, 1% $H_2SO_4$.400 ml 30 min.

The dried agar was used as a substrate and upon completion of the reaction, saccharification yields according to the different reaction temperature were compared one another. Since the substrate was agar, the producible monosaccharides were galactose and 3,6-anhydrogalactose (3,6-AHG) (FIG. 2). But, only the monosaccharide that can be easily fermented was selected, which was galactose, to calculate the yield. 10 g of the substrate and 400 ml of sulfuric acid aqueous solution were added into a 500 ml reactor, followed by reaction at 80-120° C. for 30 minutes. After completion of the reaction, the temperature was lowered to room temperature and the hydrolyzate was neutralized and analyzed with HLPC (ICS-3000, Dionex Co., USA). FIG. 3 illustrates the galactose yields produced from agar at different reaction temperatures. The galactose yield increased as the reaction temperature was raised from 80° C. to 120° C. But, the yield was reduced at 150° C., which suggests that even if the galactose yield increases as reaction temperature rises, once the temperature is over the upper cut the generated sugar becomes decomposed as time goes on leading to reducing the yield. Therefore, before the temperature reached 150° C., samples need to be taken out to check the yield during the reaction. And the sampling was performed when temperature reached 120, 140, and 150° C.

Figure 4:
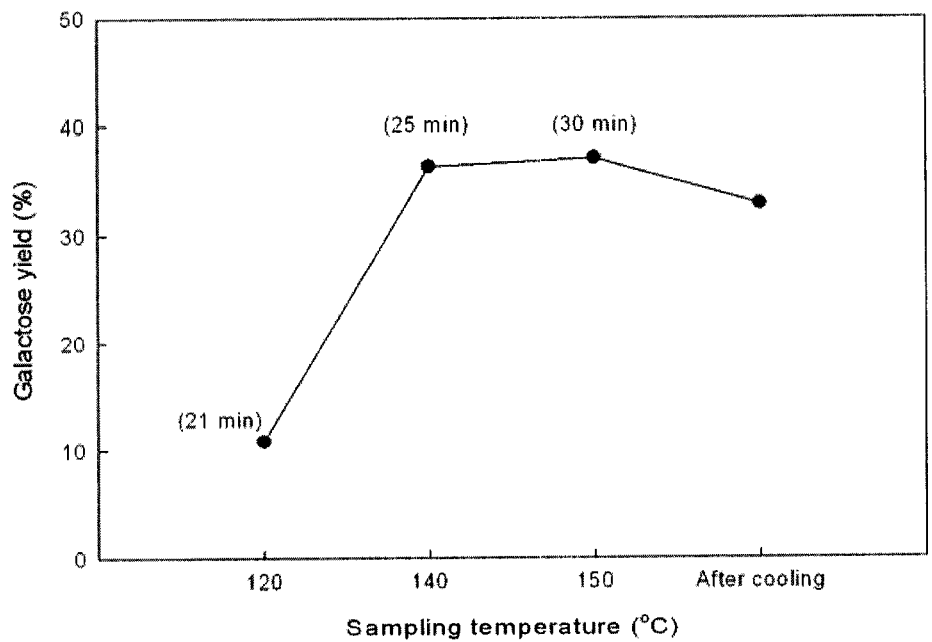
FIG. 4 is a graph showing the effects of sampling temperatures on the galactose yields using agar as a substrate. Experimental conditions: substrate 10 g, 1% $H_2SO_4$.400 ml at the point reached to corresponding temperature.

FIG. 4 illustrates the galactose yields produced from agar at the temperature of 120, 140, and 150° C. The galactose yield increased with the increase of the reaction temperature and when the temperature reached 150° C., the yield was the highest (37.1%, galactose-based: 74.2%). The yield was reduced after the reaction temperature was lowered to room temperature (32.8%), suggesting that the generated sugar was decomposed during the cooling down.

<2-1-2> Saccharification Using Cellulose

Figure 5:
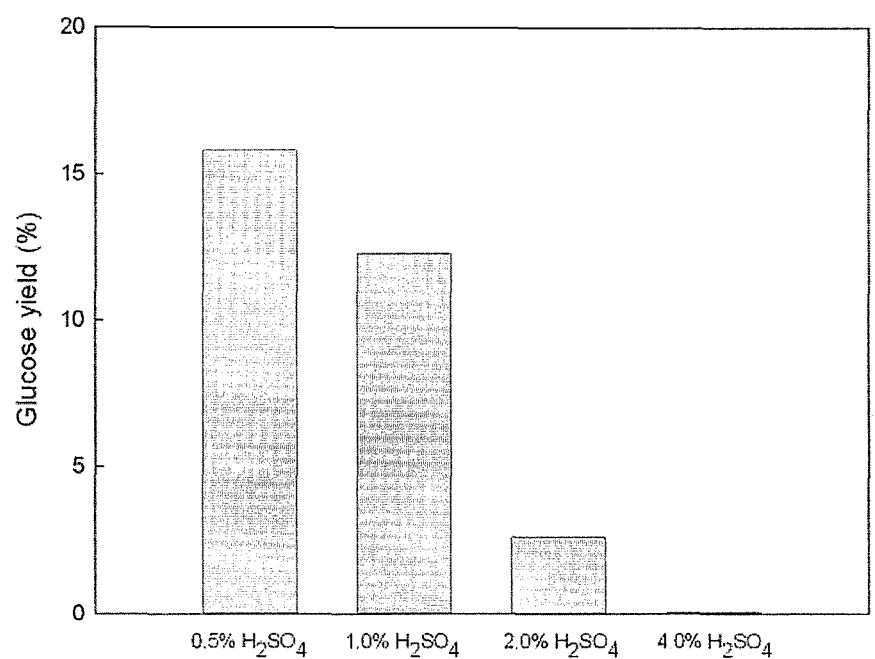
FIG. 5 is a graph showing the effects of $H_2SO_4$ concentrations on the glucose yields using cellulose as a substrate. Experimental conditions: substrate 20 g, 200° C.

Cellulose is hydrolyzed under more severe conditions. Conventionally, the crystalline structure of cellulose should be hydrolyzed even at 200-240° C. In this example, the reaction temperature was set at 200° C., considering the above, and 0.5-4.0% sulfuric acid was used as a catalyst to compare the yield of sugar over the catalyst concentrations. 20 g of the substrate and 400 ml, of sulfuric acid aqueous solution were added to a reactor, followed by saccharification for 1 hour. FIG. 5 is a graph illustrating the yields of glucose produced from cellulose over the catalyst concentrations, measured at the reaction temperature of 200° C.

As shown in FIG. 5, the yield decreased with the increase of the sulfuric acid concentration. Particularly, when 4.0% was used, the yield was only 0.1%. The yield with 2.0% sulfuric acid was 2.6%, the yield with 1.0% sulfuric acid aqueous solution was 12.3%, and the yield with 0.5% sulfuric acid was found to be 15.8%.

<2-2> Enzymatic Hydrolysis

The substrate (agar: 1.1 g, cellulose: 2.5 g) and 100 ml of distilled water were mixed in a 250 ml Erlenmeyer flask. pH was regulated according to the selected enzyme. After adding 1 ml of each enzyme, saccharification was performed with mixing at 100 rpm under the reaction conditions appropriate for each enzyme selected. Samples were taken during the reaction at regular intervals and the samples were centrifuged using a centrifuge (VS-150FN, Vision Science Co., LTD., Korea) at 3,000 rpm for 5 minutes and supernatant obtained was analyzed.

Saccharification using cellulose as a substrate was performed with the primary substrate concentration of 2.5% for 144 hours. As shown in Table 5, the glucose concentration resulted from the saccharification was 11.6 g/l, suggesting that approximately 46% of the cellulose was converted into glucose. Saccharification was rapidly induced for the first 3 hours and then the reaction became slow but consistent. Considering the maximum conversion rate of cellulose into glucose by acid-hydrolysis was 15% (FIG. 7), the saccharification by cellulase is believed to be very efficient.

The solution containing agar at least by 1% was very sticky. Thus, saccharification using agar as a substrate was performed with the primary substrate concentration of 1.1% for 144 hours. As a hydrolytic enzyme, the commercialized enzyme mixture of amylolytic enzyme, maltase and lactase was used considering economic efficiency. As a result, as shown in Table 6, the amylolytic enzyme including amylase was found to be not effective in agar hydrolysis, and galactose detected in the early reaction stage was believed to be free galactose monomers isolated from the agar composition separation process.

TABLE 5

Glucose concentration from cellulose as a substrate by enzymatic saccharification

| | | Glucose concentration (g/l) | | | | | | |
|---|---|---|---|---|---|---|---|---|
| Substrate | Enzyme | 0 h | 3 h | 6 h | 24 h | 48 h | 72 h | 144 h |
| Cellulose | celluclast | 0.44 | 7.68 | 7.94 | 9.64 | 9.63 | 10.23 | 11.6 |

TABLE 6

Galactose concentration from agar as a substrate by enzymatic saccharification

| | | Galactose concentrations (g/l) | | | | | | |
|---|---|---|---|---|---|---|---|---|
| Substrate | Enzyme | 0 h | 3 h | 6 h | 24 h | 48 h | 72 h | 144 h |
| Agar | viscozyme | 1.18 | 3.1 | 1.73 | 1.19 | 1.19 | 1.37 | 1.38 |
| | spirizyme | 0.23 | 1.36 | 0.24 | 0.25 | 0.24 | 0.43 | 0.44 |
| | AMG | 0.27 | 0.28 | 0.28 | 0.28 | 0.28 | 0.47 | 0.47 |
| | Lactozym | 0 | 0 | 0 | 0 | 0 | 0.57 | 0.37 |

<2-3> Direct Saccharification
<2-3-1> Effects of Temperature and Time
<2-3-1-1> S/L Ratio 5.5%

Figure 6:
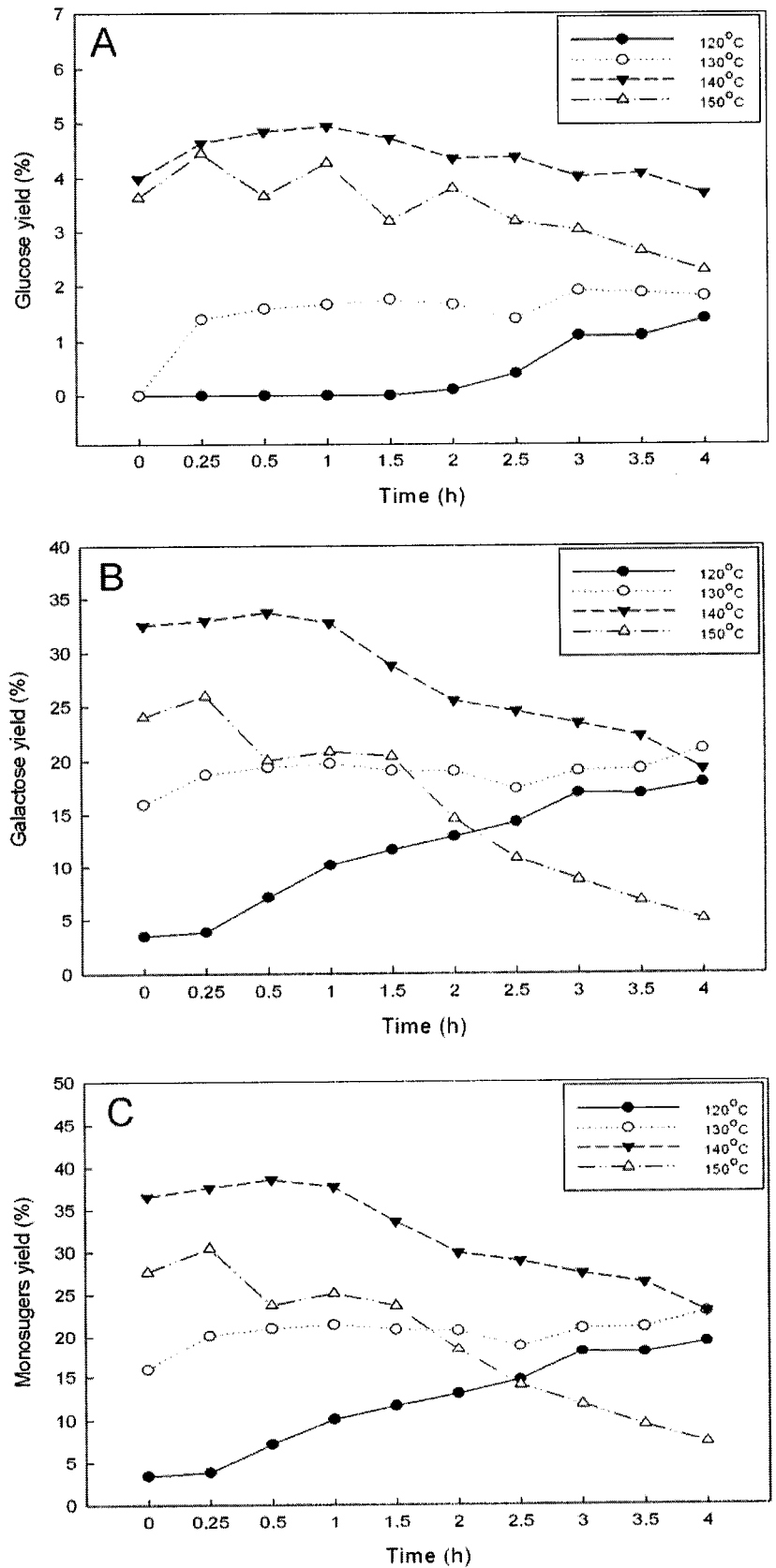
FIG. 6 is a graph showing the effects of reaction temperature and reaction time on the monosugars yields using *Gelidium amansii* as a substrate. (A) glucose yield, (B) galactose yield, (C) glucose+galactose yield. Experimental conditions: substrate 22 g, 1% $H_2SO_4$ 400 ml.

22 g of *Gelidium amansii* from Morocco, the substrate, was mixed with 400 ml of 1% sulfuric acid aqueous solution, followed by saccharification at 120-150° C. for 4 hours. The yields of glucose, galactose and glucose+galactose (monosugars) were investigated over the reaction temperature and time with the S/L ratio of 5.5%. As a result, as shown in FIG. 6, glucose and galactose exhibited the highest yields at 140° C. (glucose: 4.8%, galactose: 33.7%, monosaccharides: 38.5%), and the yields increased as the reaction time at 120° C. The yield of galactose was rapidly decreased after 15 minutes of reaction at 150° C.

<2-3-1-2> S/L Ratio 10.0%

Figure 7:
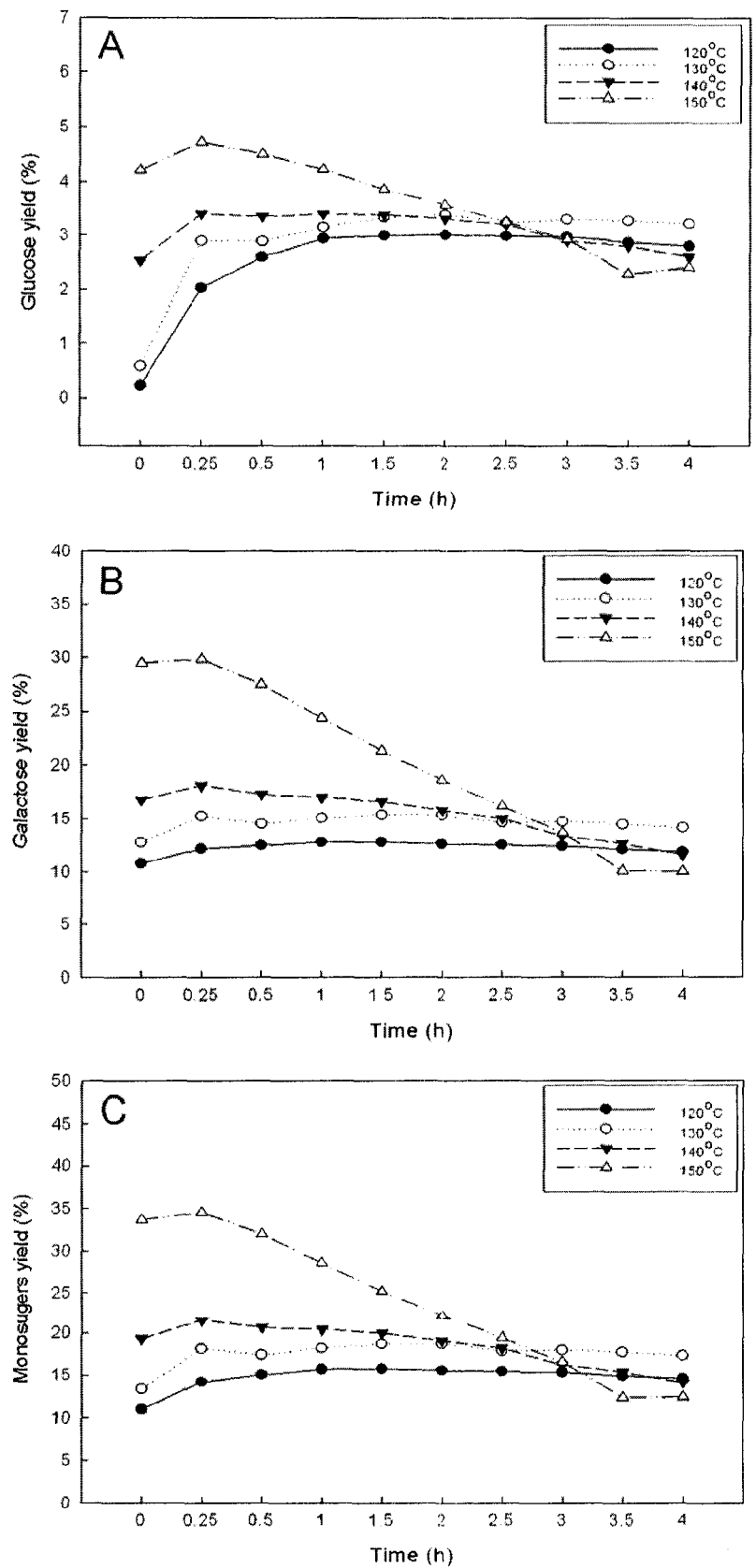
FIG. 7 is a graph showing the effects of reaction temperature and reaction time on the monosugars yields using *Gelidium amansii* as a substrate. (A) glucose yield, (B) galactose yield, (C) glucose+galactose yield. Experimental conditions: substrate 40 g, 1% $H_2SO_4$ 400 ml.

40 g of *Gelidium amansii* from Morocco, the substrate, was mixed with 400 ml of 1% sulfuric acid aqueous solution, followed by saccharification at 120-150° C. for 4 hours. FIG. 7 is a graph illustrating the yields of glucose, galactose and glucose+galactose (monosugars) over the reaction time and temperature at the S/L ratio of 10.0%. The yields of glucose and galactose were both the highest at 150° C. and the reaction time for giving the highest yield was found to be 15 minutes (glucose: 4.7%, galactose: 29.8%, monosugars: 34.5%).

<2-3-1-3> S/L Ratio 15.0%

Figure 8:
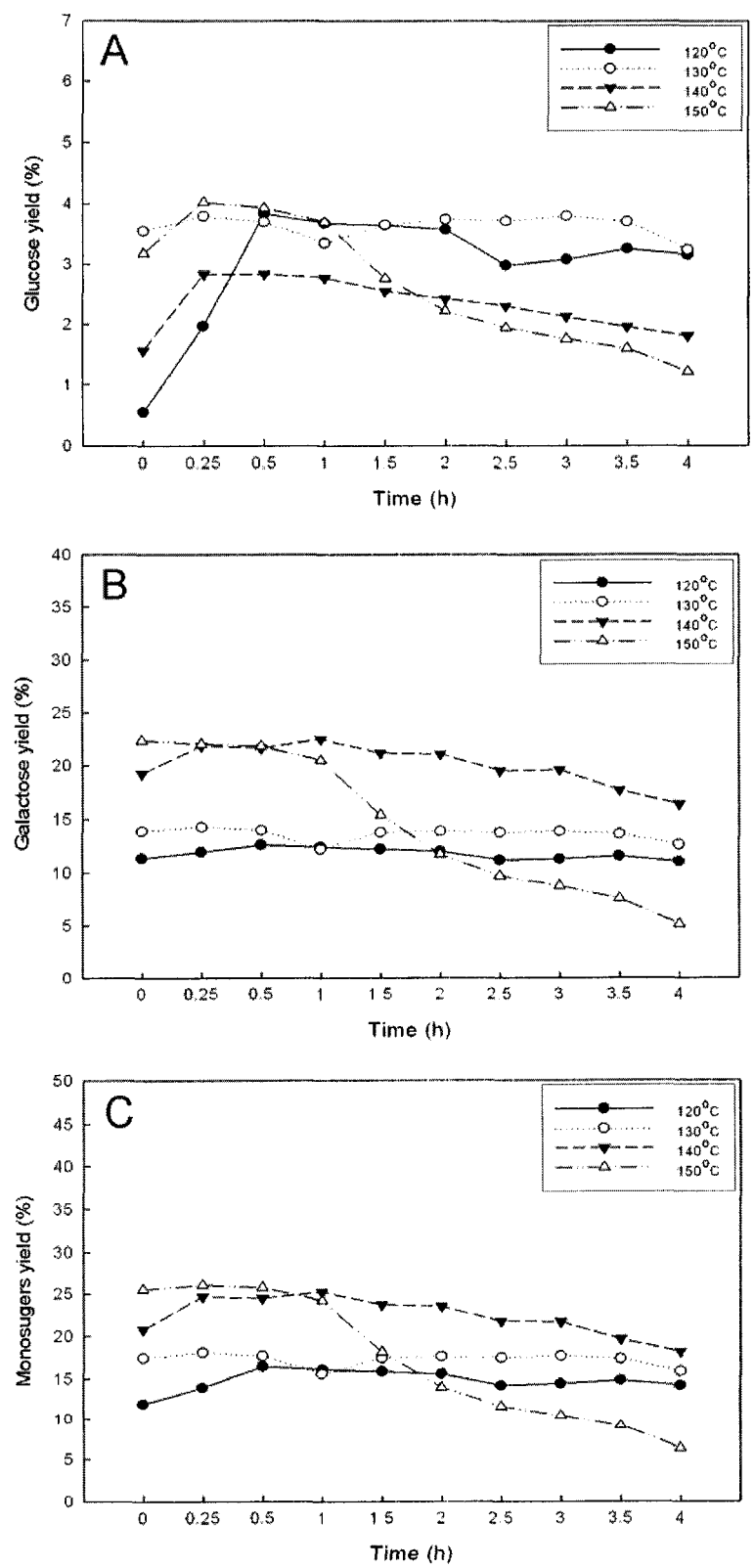
FIG. 8 is a graph showing the effects of reaction temperature and reaction time on the monosugars yields using *Gelidium amansii* as a substrate. (A) glucose yield, (B) galactose yield, (C) glucose+galactose yield. Experimental conditions: substrate 60 g, 1% $H_2SO_4$ 400 ml.

FIG. 8 is a graph illustrating the yields of glucose, galactose and glucose+galactose (monosugars) over the reaction time and temperature with the S/L ratio of 15.0% (substrate: 60 g, 1% sulfuric acid aqueous solution: 400 ml). At the S/L ratio of 15.0%, the reaction temperature and time for the highest yields were 150° C. and 0-15 minutes (glucose: 4.0%, galactose: 22.0%, monosugars: 26.0%). Hydrolysis was hardly induced after 30 minutes at 120-140° C., which was consistent result with when the S/L ratio was 10.0%.

<2-3-2> Effect of S/L ratio

Figure 9:
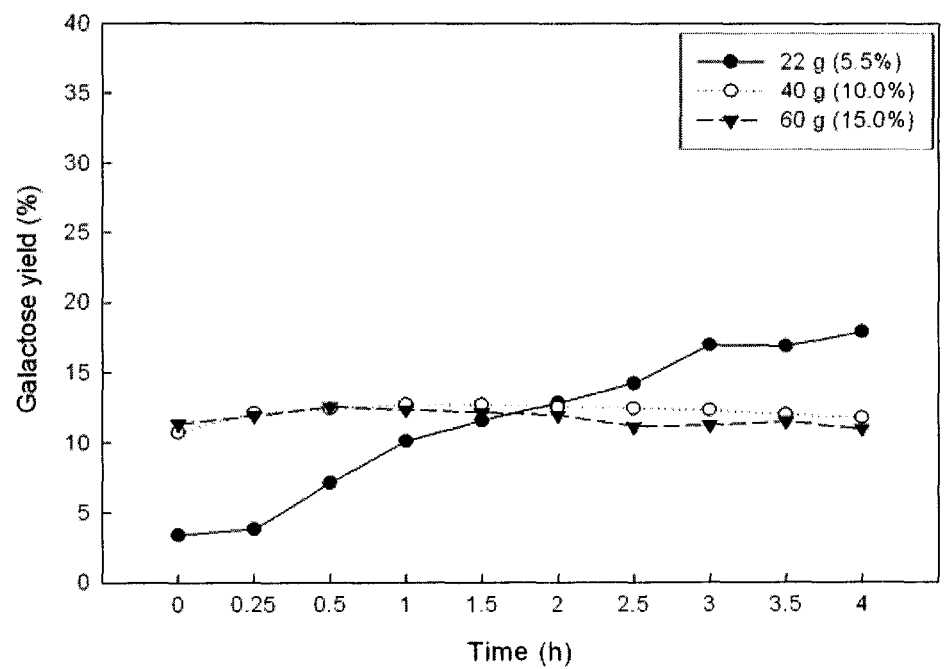
FIG. 9 is a graph showing the effects of S/L ratios on the galactose yield using *Gelidium amansii* as a substrate. Experimental conditions: 1% $H_2SO_4$ 400 ml, 120° C., 4 h.

FIG. 9 illustrates the yields of galactose resulted from saccharification at 120° C. for 4 hours at different S/L ratios. To minimize the factors of the S/L ratio and the reaction temperature affecting yields, the results of the lowest reaction temperature (120° C.) were compared. Since the yield of glucose was too low to be considered, only galactose yield is showed in FIG. 9, resulting that the S/L ratio of 5.5% showed the highest galactose yields. Those had similar yields (11~13%) at the S/L ratios of 10.0% and 15.0%.

<2-3-3> Effect of Acid Concentration

Figure 10:
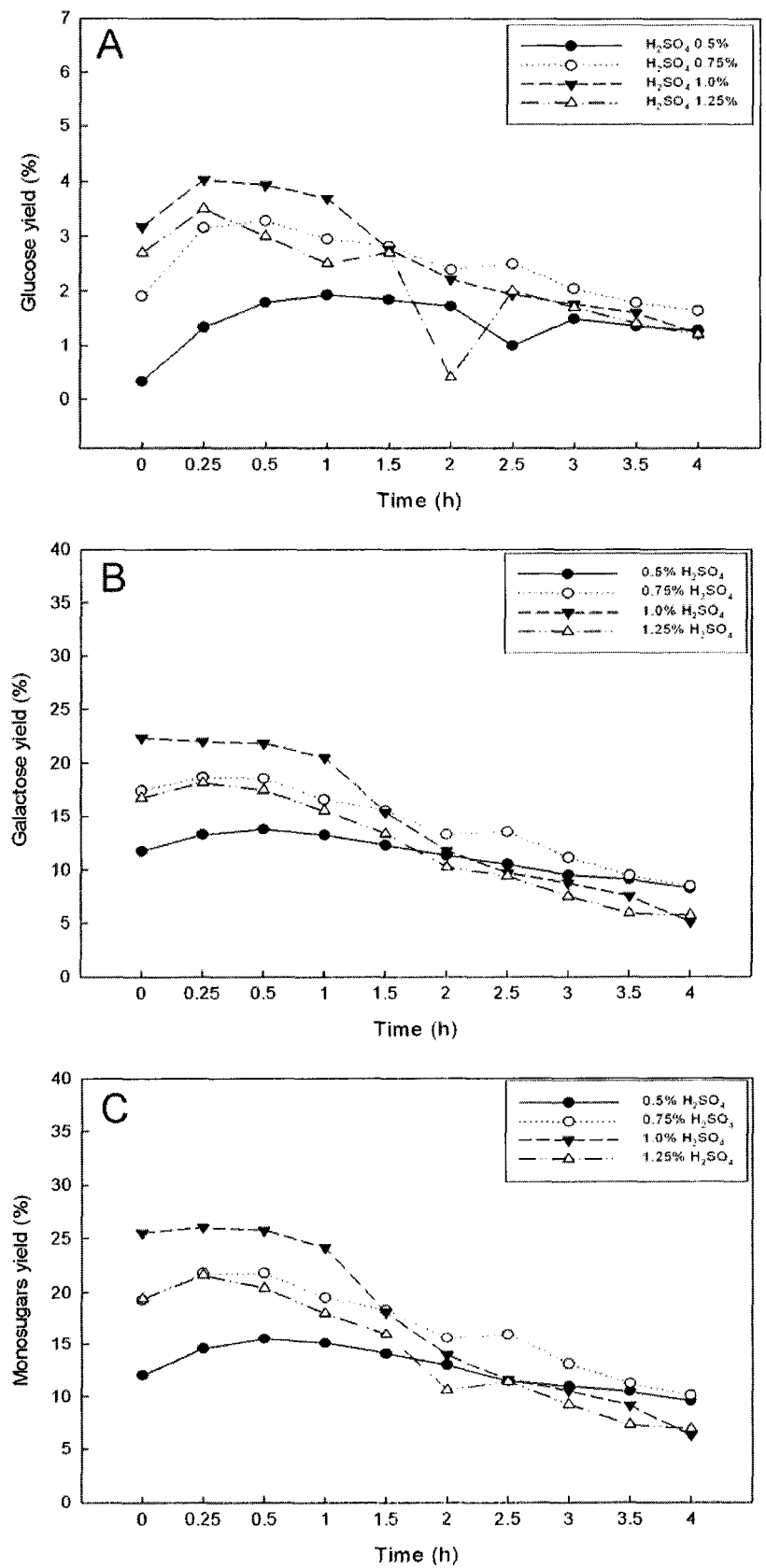
FIG. 10 is a graph showing the effects of $H_2SO_4$ concentrations on the monosugars yields using *Gelidium amansii* as a substrate. (A) glucose yield, (B) galactose yield, (C) glucose+galactose yield. Experimental conditions: substrate 60 g, 150° C., 4 h.

To compare the monosugar yields using *Gelidium amansii* as a substrate according to the catalyst concentrations, 60 g of the substrate was mixed with 400 ml of 0.5-1.25% sulfuric acid solution, followed by saccharification at 150° C. for 4 hours. As shown in FIG. 10, when saccharification was performed with 1.0% sulfuric acid solution for 0-15 minutes, the yield of glucose was 4.0% and the yield of galactose was 22.3%, which were the highest, but after 15 minutes the yields were reduced. When saccharification was performed with 0.75-1.25% sulfuric acid solution, the yield started decreasing after one hour. When 0.5% sulfuric acid solution was used, the yields over the reaction time were not much different. When 0.75% or 1.25% sulfuric acid solution was used, the yields between the two were almost same and when 0.5% sulfuric acid solution was used, the yield was the lowest.

<2-3-4> Effect of the Kind of Acid

Figure 11:
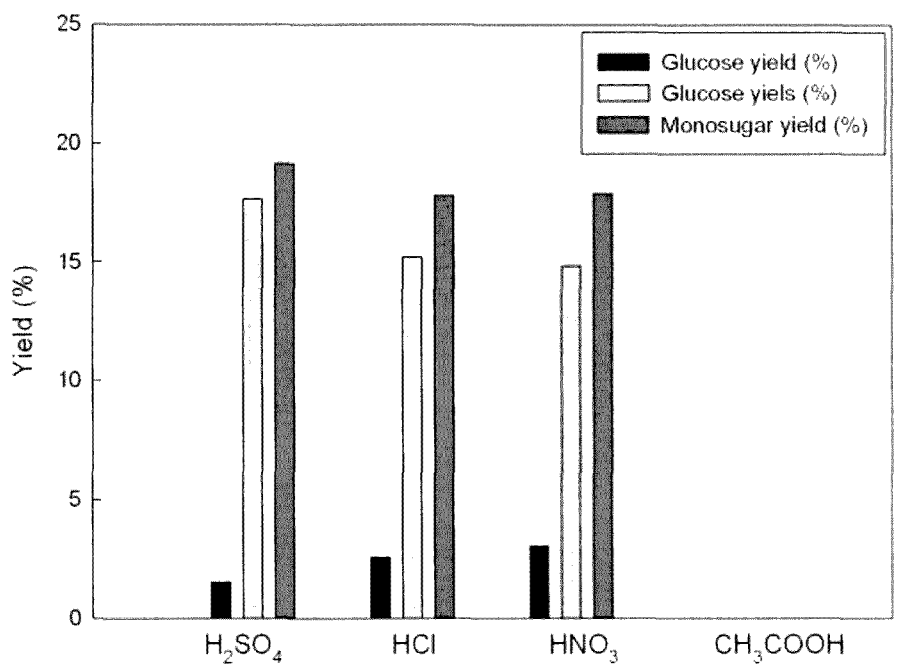
FIG. 11 is a graph showing the effect of acid types on the monosugars yield using *Gelidium amansii* as a substrate. (A) glucose yield, (B) galactose yield, (C) glucose+galactose yield. Experimental conditions: substrate 7.5 g, 1% $H_2SO_4$, 200 ml, 121□, 15 min.

To compare the yields of produced monosugars according to the kinds of acid, 7.5 g of *Gelidium amansii* from Morocco and 200 ml of 1% sulfuric acid, hydrochloric acid, nitric acid, and acetic acid aqueous solution were put in a 250 ml Erlenmeyer flask, followed by saccharification in a autoclave at 121° C. for 15 minutes. FIG. 11 shows the yields of glucose, galactose and glucose+galactose (monosugars) produced with the above catalysts. Particularly, when acetic acid was used as a catalyst, hydrolysis was not induced, suggesting that acetic acid is not a proper catalyst for acid-hydrolysis. Whereas the sulfuric acid was used as a catalyst, the yields of galactose and glucose were both high.

<2-4> Multi-Step Saccharification

In the previous experiments, it was confirmed that the conditions for hydrolysis to yield galactose and glucose were found to be different from each other. Particularly, the conditions for hydrolysis of agar to galactose were much more moderate, compared with the conditions for cellulose to glucose. It was also confirmed that the yield of the produced monosugars was much higher when the saccharification was induced with cellulose and agar separated from *Gelidium amansii* than when induced with *Gelidium amansii* directly. So, if saccharification efficiency is maximized by modifying the process, the production of ethanol will be maximized.

Figure 12:
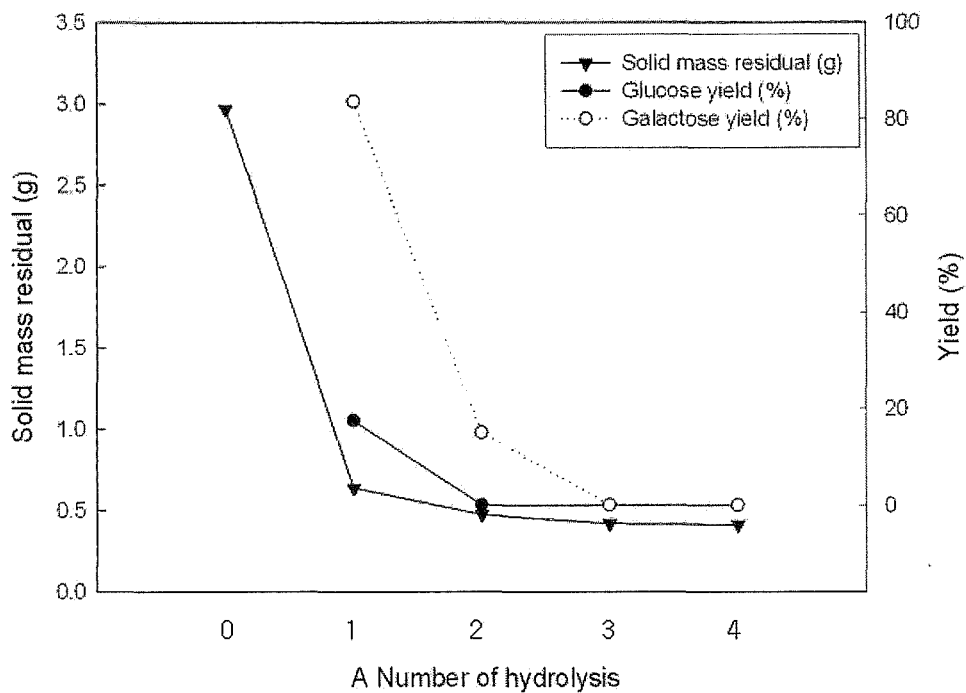
FIG. 12 is a graph showing the effects of number of hydrolysis on the monosugars yields using *Gelidium amansii* as a substrate. Experimental conditions: 1% $H_2SO_4$, 121° C., 15 min.

In this example, 7.5 g of *Gelidium amansii* from Morocco was mixed with 200 ml of 1% sulfuric acid aqueous solution in a 250 ml Erlenmeyer flask, followed by saccharification in a autoclave at 121° C. for 15 minutes and the reaction performed stepwise, like the first, the second, the third and the forth saccharification. The glucose extraction yield and the yields of glucose and galactose over the steps were investigated. As a result, as shown in Table 7 and FIG. 12, the extraction yield after the first saccharification was 78.0% (cellulose content in *Gelidium amansii*: 17%, The yield was calculated considering the cellulose content and presented as the ratio to the total amount of the raw material). The yield of galactose after the second saccharification was 29.6%, which was raised to 105.7% when the ratio was calculated considering not the total amount of the raw material but hydrolysable component (28%, see Table 4) into galactose only (the reason why the yield was more than 100%: some of 3,6-AHG were converted into galactose). Almost all the galactose of *Gelidium amansii* was extracted. The yield of glucose after the first saccharification did not increase by the repeated saccharification thereafter, suggesting that hydrolysis of cellulose was not induced any more. Till the second saccharification under the above reaction conditions, the processes of saccharification of agar into galactose and separation of cellulose from *Gelidium amansii* went on efficiently. If the yield of glucose from the separated cellulose could increase by acid-hydrolysis or enzymatic hydrolysis, the multi-step saccharification can be effectively used as the optimum method capable of maximizing monosugar yields.

TABLE 7

Effects of number of hydrolysis on the monosugars yields using *Gelidium amansii* as substrate (condition: 1% $H_2SO_4$, 121° C., 15 min)

| Number of hydrolysis | Solid mass residual (g) | Reduced rate (%) | Glucose yield (%) | Galactose yield (%) |
|---|---|---|---|---|
| 0 | 2.9670 | — | — | — |
| 1st | 0.6397 | 78.4 | 3.5 | 25.1 |
| 2nd | 0.4752 | 5.5 | Not detected | 4.5 |
| 3rd | 0.4207 | 1.8 | Not detected | Not detected |
| 4th | 0.4128 | 0.3 | Not detected | Not detected |

Example 3

Ethanol Producing Strain Culture

<3-1> Characteristics of Strains

<3-1-1> *Saccharomyces Serevisiae*

Figure 13:
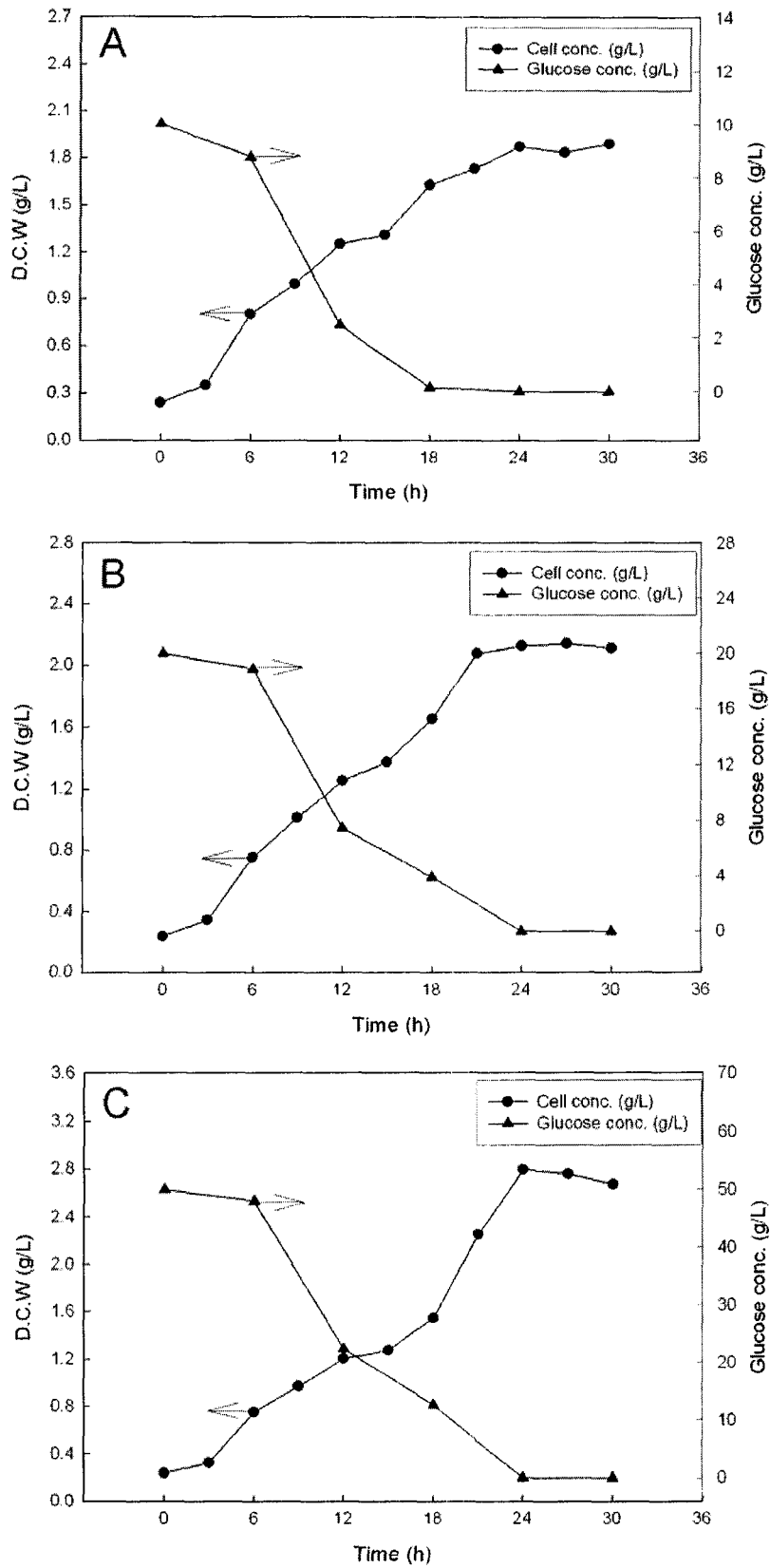
FIG. 13 is a graph showing the growth curve of *S. cerevisiae* under various glucose concentrations. (A) 1.0%, (B) 2.0%, (C) 5.0%.
Figure 14:
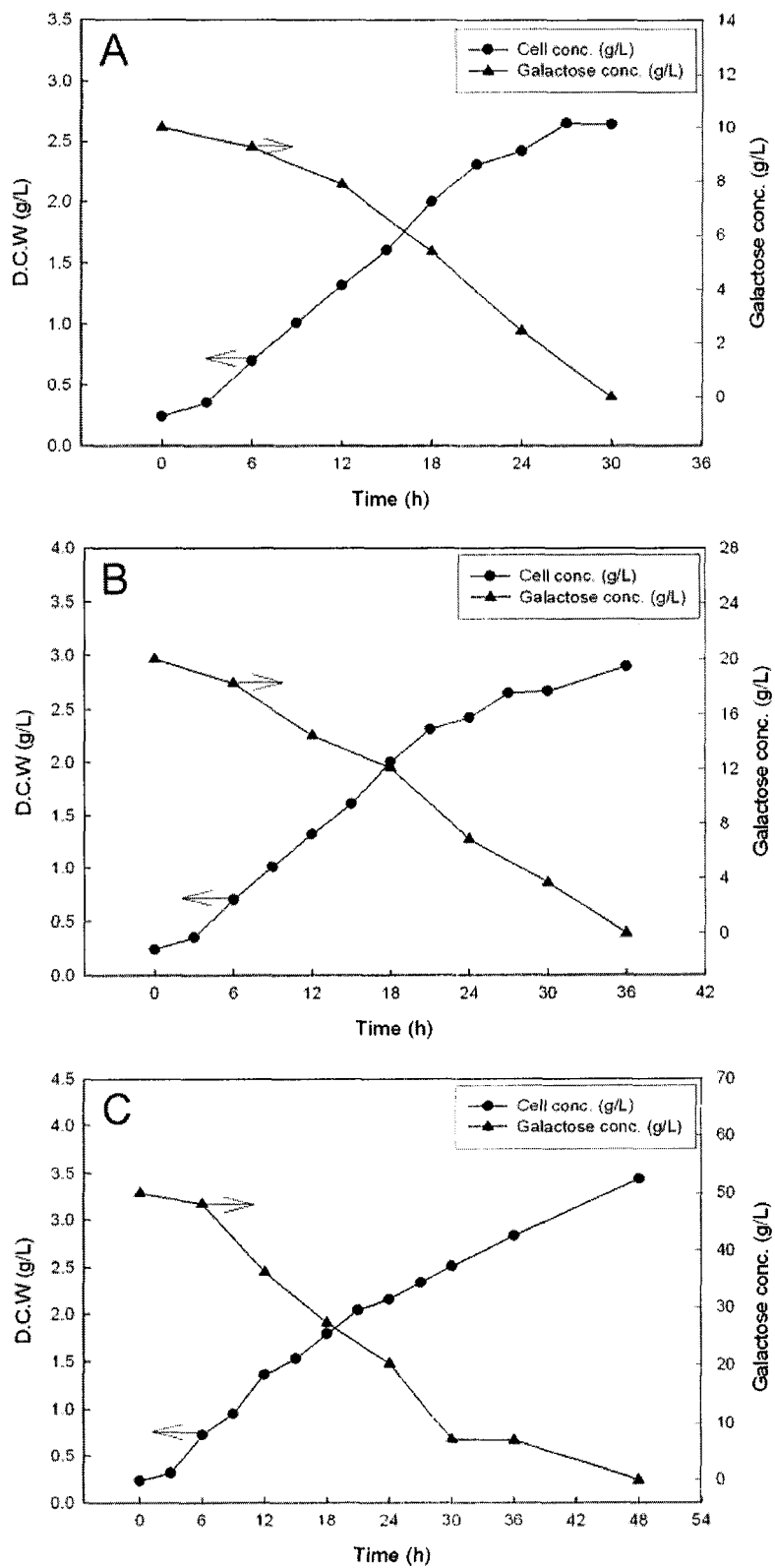
FIG. 14 is a graph showing the growth curve of *S. cerevisiae* under various galactose concentrations. (A) 1.0%, (B) 2.0%, (C) 5.0%.

To investigate the growth pattern and sugar uptake of the ethanol producing yeast, *Saccharomyces serevisiae*, glucose and galactose were used as carbon sources for the culture. At this time, the culture was performed with different carbon source concentrations of 1%, 2% and 5%. FIG. 13 illustrates the growth curve and sugar uptake of *Saccharomyces serevisiae* when glucose was used at different concentrations of 1%, 2% and 5%. FIG. 14 illustrates the growth curve and sugar uptake of *Saccharomyces serevisiae* when galactose was added at different concentrations of 1%, 2% and 5%. As the concentration of the carbon source increased, the concentration of cells increased. With the highest concentration of carbon source (5%), the growth rate of the yeast was lower than expected. Regardless of the concentration of the carbon source, glucose was all consumed within 24 hours and galactose was all consumed within 48 hours. The consumption of glucose was faster than the consumption of galactose, but the growth of the yeast was higher when galactose was used as a carbon source than when glucose was used.

<3-1-2> *Brettanomyces Custersii*

Figure 15:
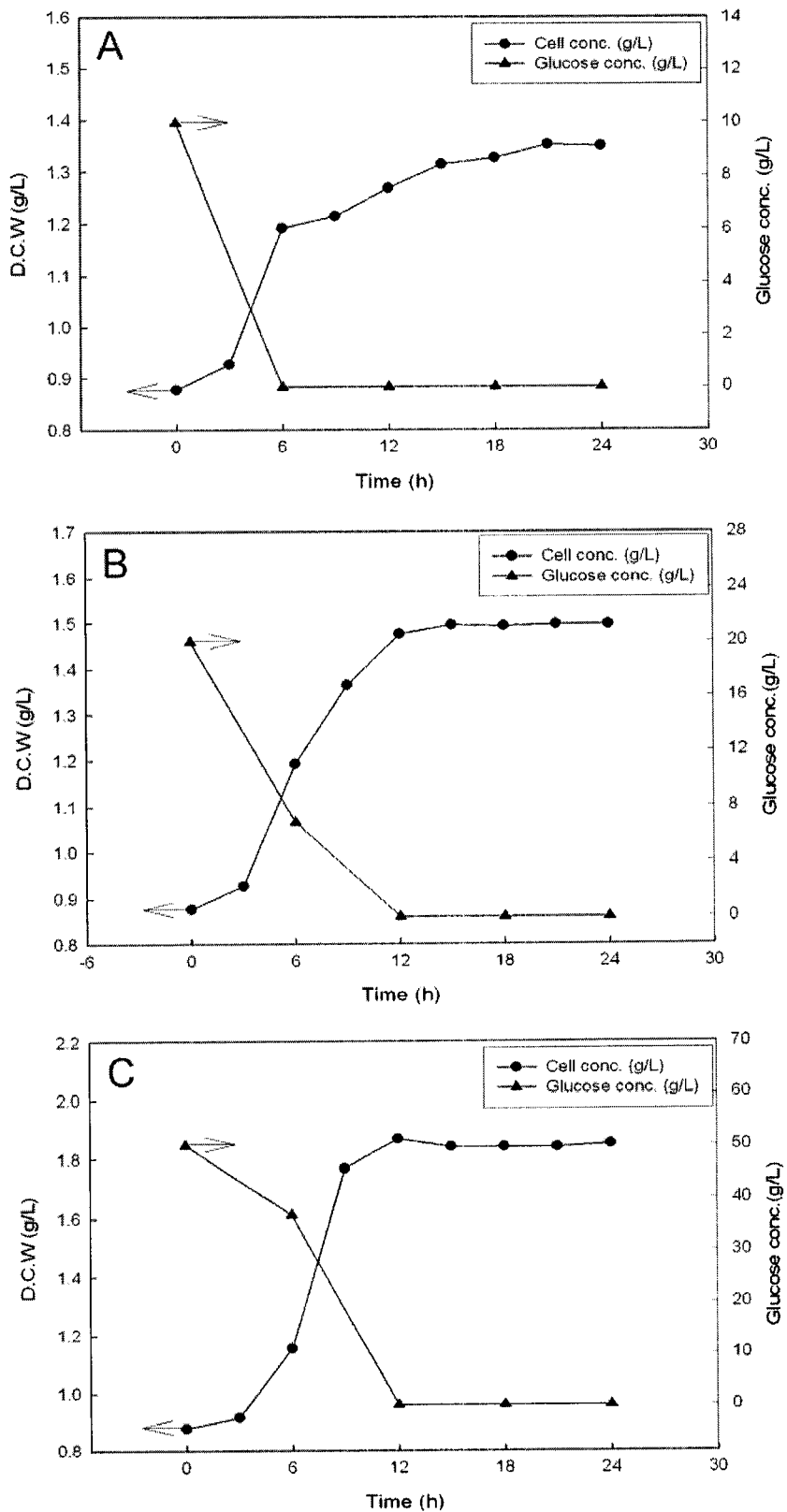
FIG. 15 is a graph showing the growth curve of *B. custersii* under various glucose concentrations. (A) 1.0%, (B) 2.0%, (C) 5.0%.
Figure 16:
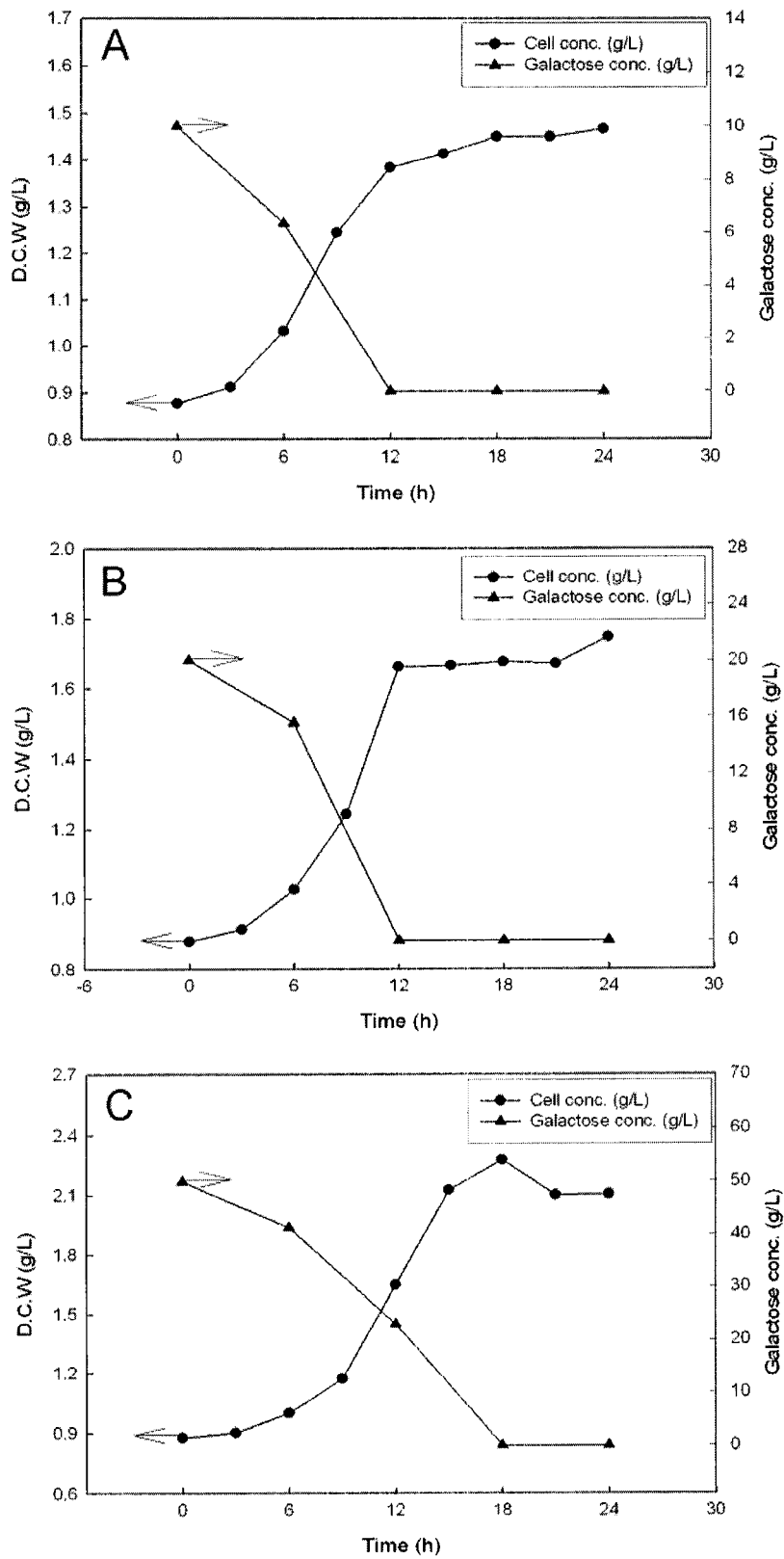
FIG. 16 is a graph showing the growth curve of *B. custersii* under various galactose concentrations. (A) 1.0%, (B) 2.0%, (C) 5.0%.

The growth pattern and sugar uptake of another ethanol producing yeast, *Brettanomyces custersii*, were investigated with the same carbon source and concentrations as used for the culture of *Saccharomyces serevisiae*. As a result, as shown in FIG. 15 and FIG. 16, the concentration of the strain increased with the increase of the concentration of the carbon source and when galactose was used as a carbon source, the mycelial concentration of the yeast was found to be the highest when 5% of galactose was used. The result was consistent with that of *Saccharomyces serevisiae*. It was also consistent that glucose consumption was faster than galactose consumption in the case of *Brettanomyces custersii* regardless or the carbon source concentrations, precisely all the glucose were consumed within 12 hours and all the galactose were consumed within 18 hours, suggesting that sugar uptaking speed was twice as fast as that of *Saccharomyces serevisiae*. The growth rate of the strain was also faster than that of *Saccharomyces serevisiae*.

<3-2> Ethanol Fermentation

*Saccharomyces cerevisiae* and *Brettanomyces custersii*, the yeasts being preserved in solid media, were inoculated in a 250 ml, Erlenmeyer flask containing 100 ml of YEPD by using a platinum loop, followed by pre-culture at 37° C. or 30° C. at 150 rpm for 24 hours, respectively. Main culture followed at 37° C. or 30° C. for 48 hours under the primary pH 5.0-5.5 after inoculating 25% of the pre-culture solution in 150 ml (if inoculating into a fermentor, the volume would be 2.5 l) of medium containing mixed sugar or hydrolyzate (1-20%) and peptone 15%, yeast extract 15%, and magnesium sulfate 0.5%.

<3-2-1> Fermentation Using Mixed Sugar

Figure 17:
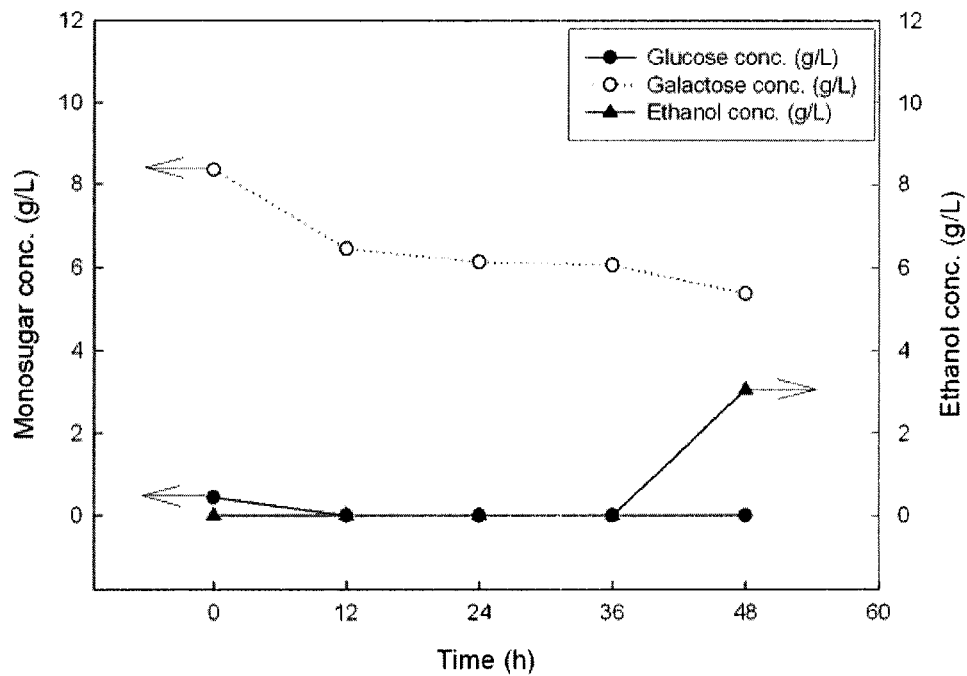
FIG. 17 is a graph showing the ethanol production by *S. cerevisiae* using mixed sugar.
Figure 18:
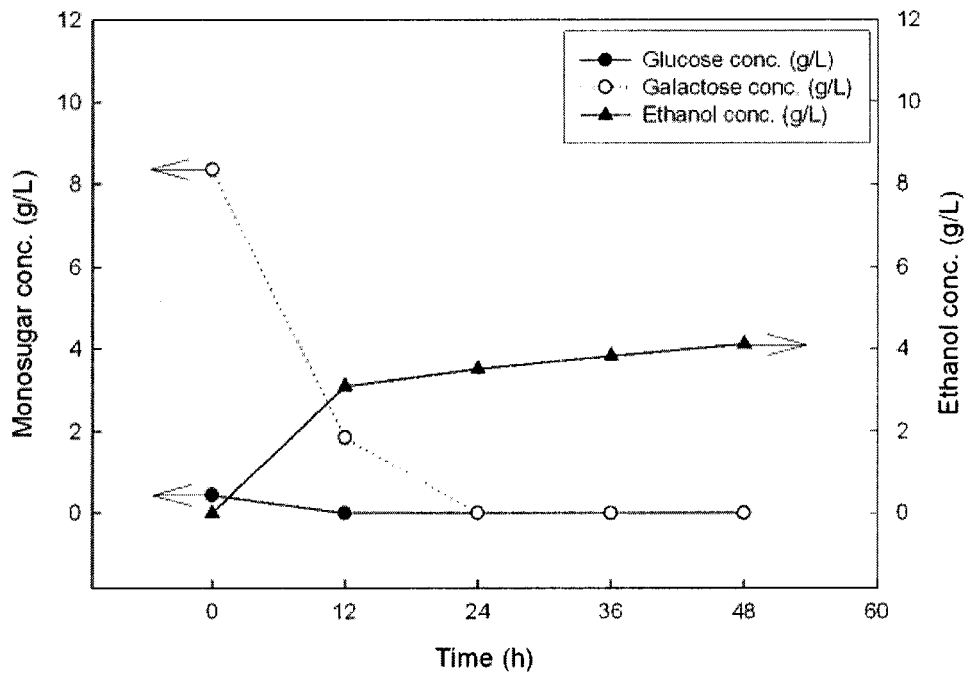
FIG. 18 is a graph showing the ethanol production by *B. custersii* using mixed sugar.

After the first saccharification of *Gelidium amansii* in an autoclave at 121° C. for 15 minutes, the galactose concentration was 0.8-0.9%, and the glucose concentration was 0.03-0.05%. In this example, a mixed sugar was prepared using the same concentration as the hydrolyzate and the same ratio of (galactose/glucose) as well. Then, ethanol fermentation patterns of *Saccharomyces cerevisiae* and *Brettanomyces custersii* using the mixed sugar were investigated. FIG. 17 and FIG. 18 illustrate the results of ethanol fermentation using *Saccharomyces cerevisiae* and *Brettanomyces custersii* as fermentation yeasts in the mixed sugar. *Saccharomyces serevisiae* did not consume all the mixed sugar even after 48 hours of fermentation (consumed all glucose but consumed only 35% of galactose), and it consumed glucose first and after consuming all the glucose it started consuming galactose for metabolism. In the meantime, *Brettanomyces custersii* used both glucose and galactose simultaneously for its metabolism and consumed all the mixed sugar within 24 hours of fermentation. This strain started producing ethanol from the start of fermentation (triggered by glucose) and 48 hours later it produced approximately 4.1 g/l ethanol (ethanol yield: 93.8%). When *Brettanomyces custersii* was used as a fermentation yeast, ethanol level was continuously increased even after the carbon source was all consumed after 24 hours of fermentation, suggesting that intracellular composition was converted.

<3-2-2> Fermentation Using Hydrolyzate

Figure 19:
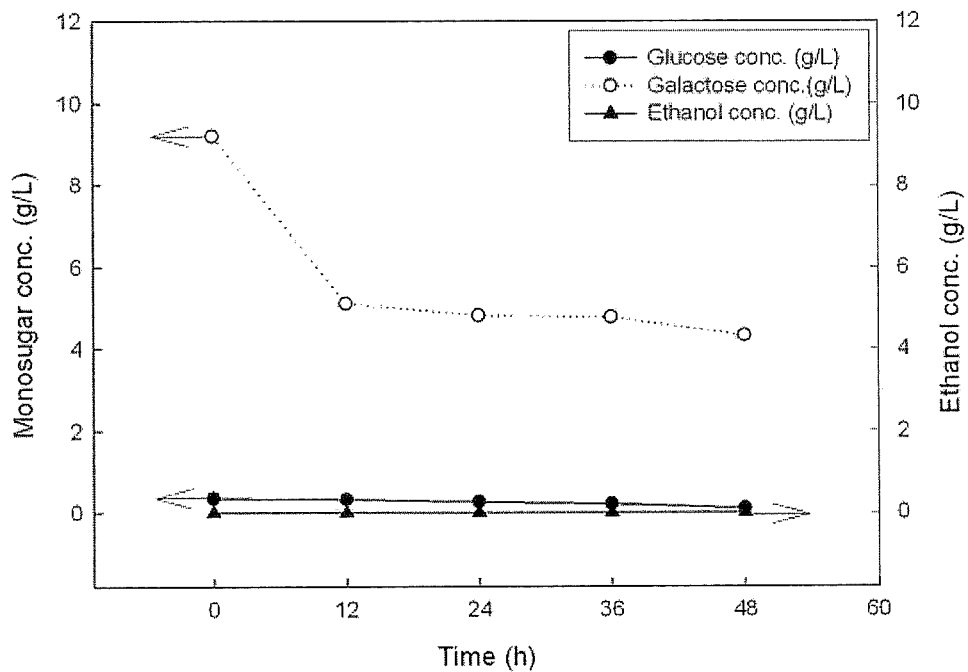
FIG. 19 is a graph showing the ethanol production by *S. cerevisiae* using hydrolyzate.
Figure 20:
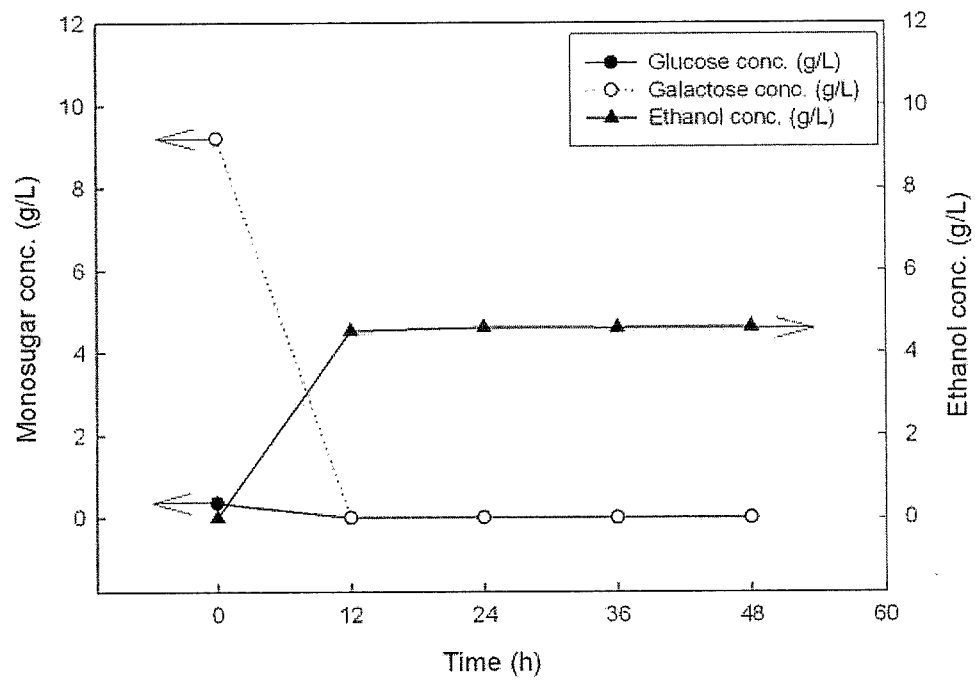
FIG. 20 is a graph showing the ethanol production by *B. custersii* using hydrolyzate.

FIG. 19 and FIG. 20 illustrate the results of ethanol fermentation using *Saccharomyces cerevisiae* and *Brettanomyces custersii* as fermentation yeasts using the hydrolyzate hydrolyzed in an autoclave. *Saccharomyces serevisiae* did not produce ethanol even after 48 hours of fermentation, whereas *Brettanomyces custersii* produced ethanol (4.6 g/l, ethanol yield: 96.0%) after 12 hours of fermentation but not any more since then. Compared with the results of using the mixed sugar, both *Saccharomyces serevisiae* and *Brettanomyces custersii* demonstrated slower sugar consuming rate and less ethanol production.

INDUSTRIAL APPLICABILITY

As explained hereinbefore, the method of producing biofuel using marine algae of the present invention contributes to the improvement of raw material supply by using abundant marine biomass, the decrease of production costs by excluding lignin eliminating process that is necessary when wood-based material is used according to the conventional method, the decrease of production costs by converting most of carbohydrates included in the marine algae such as galactose, 3,6-anhydrogalactose as well as glucose into biofuel leading to overcoming the worries of energy source, and the decrease of greenhouse gas owing to the excellent $CO_2$ absorption by marine algae. Consequently, the present invention is advantageous in economic and environmental viewpoint, and in coping with the international environmental regulations as well.

What is claimed is:

1. A method of producing biofuel comprising the following steps:
    generating monosugars selected from the group consisting of galactose, galactose derivative, and 3,6-anhydrogalactose by treating red algae selected from the group consisting of *Gelidium amansii, Cottonii* and *Gracilaria verrucosa*, or polysaccharides extracted from red algae selected from the group consisting of *Gelidium amansii, Cottonii* and *Gracilaria verrucosa* with a hydrolytic enzyme and/or a hydrolytic catalyst; wherein the extraction of the polysaccharides is performed by the following steps:
        soaking the red algae in an alkali aqueous solution and washing them with water;
        soaking the washed red algae in an extraction solvent for a predetermined time and extracting one or more polysaccharides selected from the group consisting of agar, carrageenan and alginic acid; and
        separating the extracted polysaccharides and collecting the remaining starch or cellulose; and
    fermenting the monosugars using a *Brettanomyces custersii*.

2. The method of producing biofuel according to claim 1, wherein the biofuel is selected from the group consisting of $C_1$-$C_4$ alcohol and $C_3$-$C_4$ ketone.

3. The method of producing biofuel according to claim 2, wherein the biofuel is selected from the group consisting of methanol, ethanol, propanol, butanol and acetone.

4. The method of producing biofuel according to claim 1, wherein the extraction solvent comprises an acid selected from the group consisting of $H_2SO_4$, HCl, HBr, $HNO_3$, $CH_3COOH$, HCOOH, $HClO_4$, $H_3PO_4$, and PTSA (para-toluene sulfonic acid).

5. The method of producing biofuel according to claim 1, wherein the hydrolytic enzyme is selected from the group consisting of β-agarase, β-galactosidase, β-glucosidase and endo-1,4-β-glucanase.

6. The method of producing biofuel according to claim 1, wherein the hydrolytic catalyst is selected from the group consisting of $H_2SO_4$, HCl, HBr, $HNO_3$, $CH_3COOH$, HCOOH, $HClO_4$, $H_3PO_4$, and PTSA.

7. The method of producing biofuel according to claim 1, wherein the monosugar is produced by reacting agar with a hydrolytic catalyst selected from the group consisting of $H_2SO_4$, HCl, HBr, $HNO_3$, $CH_3COOH$, HCOOH, $HClO_4$, $H_3PO_4$, and PTSA at a concentration of 0.05-30% at 60-200° C. for 0-6 hours.

8. The method of producing biofuel according to claim 1, wherein the monosugar is produced by reacting red algae with a hydrolytic catalyst selected from the group consisting of $H_2SO_4$, HCl, HBr, $HNO_3$, $CH_3COOH$, HCOOH, $HClO_4$, $H_3PO_4$, and PTSA at a concentration of 0.05-30% at 60-300° C. for 0-6 hours.

9. The method of producing biofuel according to claim 1, wherein the red algae undergoes a multi-step saccharification comprising a first saccharification step of reacting the red algae with a hydrolytic catalyst selected from the group consisting of $H_2SO_4$, HCl, HBr, $HNO_3$, $CH_3COOH$, HCOOH, $HClO_4$, $H_3PO_4$, and PTSA at a concentration of 0.05-50% at 60-300° C. for 0-6 hours to produce the monosugar; and a second saccharification step of the remaining cellulose or starch under the same reaction conditions as the first saccharification step.

* * * * *

UNITED STATES PATENT AND TRADEMARK OFFICE
CERTIFICATE OF CORRECTION

| | | |
|---|---|---|
| PATENT NO. | : 8,795,994 B2 | Page 1 of 1 |
| APPLICATION NO. | : 12/528598 | |
| DATED | : August 5, 2014 | |
| INVENTOR(S) | : Kim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 806 days.

Signed and Sealed this
Twenty-fourth Day of May, 2016

Michelle K. Lee
*Director of the United States Patent and Trademark Office*